US008298787B2

(12) United States Patent
Lim et al.

(10) Patent No.: US 8,298,787 B2
(45) Date of Patent: Oct. 30, 2012

(54) METHODS FOR ENHANCING A SECRETION EFFICIENCY OF RECOMBINANT FOREIGN PROTEIN IN YEAST EXPRESSION SYSTEM

(75) Inventors: Hyung-Kwon Lim, Yongin-si (KR); Sung-Geun Kim, Yongin-si (KR)

(73) Assignee: Mogam Biotechnology Research Institute, Gyeonggi-Do (KR)

( * ) Notice: Subject to any disclaimer, the term of this patent is extended or adjusted under 35 U.S.C. 154(b) by 890 days.

(21) Appl. No.: 12/305,768

(22) PCT Filed: Jun. 20, 2006

(86) PCT No.: PCT/KR2006/002374
§ 371 (c)(1),
(2), (4) Date: Dec. 19, 2008

(87) PCT Pub. No.: WO2007/148840
PCT Pub. Date: Dec. 27, 2007

(65) Prior Publication Data
US 2010/0184136 A1    Jul. 22, 2010

(51) Int. Cl.
*C12P 21/06* (2006.01)
*C12P 21/04* (2006.01)
(52) U.S. Cl. .............................. 435/69.1; 435/71.1
(58) Field of Classification Search .................. None
See application file for complete search history.

(56) References Cited

U.S. PATENT DOCUMENTS
6,291,205 B1 * 9/2001 Tuite et al. .................. 435/69.1

FOREIGN PATENT DOCUMENTS
WO   WO 2005/071074 A1   8/2005

OTHER PUBLICATIONS

Choi et al. ("Optimization of the expression system using galactose-inducible promoter for the production of anticoagulant hirudin in *Saccharomyces cerevisiae*," Applied Microbiology and Biotechnology, vol. 42(4), pp. 587-594 (Dec. 1994)).*
Micheletti et al. (Proteins: Structure, Function, and Genetics 53:720-730 (2003)).*
Barth et al. (WO 0003008-A2 15, Jan. 20, 2000).*
Hawkins et al. (The Journal of Biological Chemistry, 281, 13485-13492, Published on Mar. 7, 2006).*
Japanese Patent Office, Japanese Office Action issued in corresponding JP Application No. 2009-516385, dated Sep. 27, 2011.
Giuseppin et al., "Comparative Study on the Production of Guar alpha-Galactosidase by *Saccharomyces cerevisiae* SU5OB and *Hansenula polymorpha* 8/2 in Continuous Cultures," Applied Environmental Microbiology, 1993, vol. 59, No. 1, pp. 52-59.
Choi et al., "Optimization of the Expression System Using Galactose-inducible Promoter for the Production of Anticoagulant Hirudin in *Saccharomyces cerevisiae*," Applied Microbiology and Biotechnology, 1994, vol. 42, pp. 587-594.
Shusta et al., "Increasing the Secretory Capacity of *Saccharomyces cerevisiae* for Production of Single-chain Antibody Fragments," Nature Biotechnology, 1998, vol. 16, pp. 773-777.
Gasser et al., "Engineering of *Pichia pastoris* for Improved Production of Antibody Fragments," Biotechnology and Bioengineering, 2006, vol. 94, pp. 353-361.
Stagoj et al., "Fluorescence Based Assay of GAL System in Yeast *Saccharomyces cerevisiae*," FEMS Microbiology Letters, 2005, vol. 244, pp. 105-110.
Cha et al., "Selection of Optimum Expression System for Production of Kringle Fragment of Human Apolipoprotein(a) in *Saccharomyces cerevisiae*," Biotechnology and Bioprocess Engineering, 2004, vol. 9, pp. 523-527.
Romanos et al., "Foreign Gene Expression in Yeast: A Review," Yeast, 1992, vol. 8, pp. 423-488.
European Patent Office, European Search Report issued in corresponding EP Application No. 06768960.4, dated Nov. 11, 2009.

\* cited by examiner

*Primary Examiner* — Suzanne M Noakes
*Assistant Examiner* — Jae W Lee
(74) *Attorney, Agent, or Firm* — Sughrue Mion, PLLC

(57) ABSTRACT

Provided is a method for improving secretion efficiency of a recombinant foreign protein in a yeast expression system. The method includes transforming a yeast host with a recombinant foreign gene construct containing a galactose-inducible promoter, a secretion signal sequence and a gene encoding the foreign protein to construct a transformed yeast strain; and culturing the transformed yeast strain under the condition that the activity of the galactose-inducible promoter is controlled. Improved secretion efficiency of the foreign protein can be achieved by decreasing overexpression-induced insoluble precipitation of the recombinant foreign protein suffered by a conventional galactose-inducible promoter-based yeast expression system, via appropriate control of a level of galactose functioning as an inducer of the galactose-inducible promoter in cells. Due to improved secretion efficiency of the recombinant foreign protein, present invention makes a contribution to improvement in productivity of recombinant foreign proteins in the yeast expression system and reduction in production costs.

9 Claims, 5 Drawing Sheets

METHODS FOR ENHANCING A SECRETION EFFICIENCY OF RECOMBINANT FOREIGN PROTEIN IN YEAST EXPRESSION SYSTEM

This is a national stage application under 35 U.S.C. §371 of PCT/KR2006/002374 filed on Jun. 20, 2006, which is incorporated herein by reference.

TECHNICAL FIELD

The present invention relates to a method for improving secretion efficiency of a recombinant foreign protein in a yeast expression system.

BACKGROUND ART

Mass production of foreign proteins using microorganisms is the most important technical area in protein pharmaceutical industry. In order to recover and purify the desired products, recombinant foreign proteins may be expressed intracellularly or otherwise may be secreted extracellularly. Upon intracellular expression of protein overexpression of the proteins may frequently lead to intracellular accumulation of proteins in the non-active and water-insoluble form in many cases and may bring about various disadvantages of productivity-lowering factors such as cumbersome processes to disrupt solid microorganisms and complicated and difficult purification processes to separate the desired protein from various kinds of host proteins present in the cells. Whereas, extracellular secretion of the desired proteins may provide easy way to avoid difficulties and problems associated with former intracellular expression of proteins. Further, since extracellular protein secretion can be successfully achieved only after correct folding and modification of the protein following the transcription process, protein production via extracellular secretion provides a benefit capable of obtaining an active form of a soluble protein having a correct tertiary structure. Therefore, it can be said that extracellular secretion of the proteins is superior to an intracellular accumulation system of recombinant foreign proteins, in terms of protein production yield as well as protein quality control.

However, in many cases, extracellular protein secretion system in a recombinant protein expression using a strong promoter frequently suffers from significantly low levels of expression and secretion, as compared to the intracellular accumulation system. In order to overcome such disadvantages and problems of extracellular secretion, a great deal of researches have been made to enhance an extracellular secretion yield of proteins. Most of researches have focused on direct optimization of signal sequence for effective secretion of protein or finding a novel and strong secretion signal sequence (Nucleic Acids Res Suppl., 2003(3):261-2; and Biochem Cell Biol. 1993, 71:401-5).

As another approach, there have been made many studies to enhance secretion efficiency of the desired protein by facilitating the protein folding corresponding to an initial rate-limiting step upon overexpression of recombinant foreign proteins and preventing insoluble precipitation which may take place prior to extracellular secretion of the protein, via induction of overexpression of chaperones that assist in folding and water-solubilization of proteins, using molecular biology techniques (Robinson and Wittrup, Biotech. Prog., 11: 171, 1995; Robinson et al., Biotechnology, 12:381-384, 1994; and Wulfing and Plukthun, Mol. Microbiol. 12(5): 685-692, 1995).

The galactose promoter, conventionally used to induce expression of foreign recombinant proteins in yeast, is a strong inducible promoter utilizing galactose as an inducer. Even though strong induction of protein expression may be advantageous to augment intracellular accumulation or expression level of foreign proteins, this may lead to decreased secretion efficiency or cellular dysfunctions due to the occurrence of insoluble precipitation in cells at an early stage of secretion when it is desired to secrete the desired protein extracellularly. Such an event is also occasionally observed in recombinant expression systems such as E. coli expression systems and yeast expression systems. In order to overcome such shortcomings, various attempts have been made to lower an incubation temperature (Baneyx F., Curr. Opin. Biotechnol., 10: 411-421, 1999; and George Georgiou and Pascal, Curr. Opin. Biotechnol., 7: 190-197, 1996).

However, such a method of lowering the incubation temperature suffers from a disadvantage associated with increased production costs of recombinant foreign proteins due to a prolonged incubation period. Therefore, there is an urgent need in the art for the development of a method capable of enhancing secretion efficiency of recombinant foreign proteins via regulation of an activity of a galactose-inducible promoter without lowering of the incubation temperature.

To this end, based on the idea that the activity of the galactose-inducible promoter may be regulated by controlling availability of galactose in a host, the inventors of the present invention have confirmed that it is possible to improve the secretion efficiency of recombinant foreign proteins by using a mutant strain lacking a galactose permease gene involved in absorption of galactose, or by culturing the transformed yeast strain via fed-batch culture with co-feeding of a certain ratio of galactose with glucose that mediates catabolite repression. The present invention has been completed based on these findings.

DISCLOSURE OF INVENTION

Technical Problem

Therefore, the present invention has been made in view of the above problems, and it is an object of the present invention to provide a method for improving extracellular secretion efficiency of a recombinant foreign protein in a yeast expression system, by genetic modification of a yeast host strain or modification of culture conditions.

Technical Solution

In accordance with an aspect of the present invention, the above and other objects can be accomplished by the provision of a method for improving secretion efficiency of a foreign protein, comprising the steps of (a) transforming a yeast host with a recombinant foreign gene construct comprising a galactose-inducible promoter, a secretion signal sequence and a gene encoding the foreign protein to construct a transformed yeast strain; and (b) culturing the transformed yeast strain under the condition that an activity of the galactose-inducible promoter is controlled.

Advantageous Effects

A method for improving secretion efficiency of a foreign protein in accordance with the present invention can achieve improved secretion efficiency of a recombinant foreign protein by decreasing overexpression-induced insoluble precipitation of a recombinant foreign protein suffered by a conventional galactose-inducible promoter-based yeast expression system, via moderate control of a level of galactose functioning as an inducer of the galactose-inducible promoter in cells. Therefore, the method of the present invention is effective to improve the productivity of recombinant foreign proteins in the yeast expression system and reduce the production costs.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
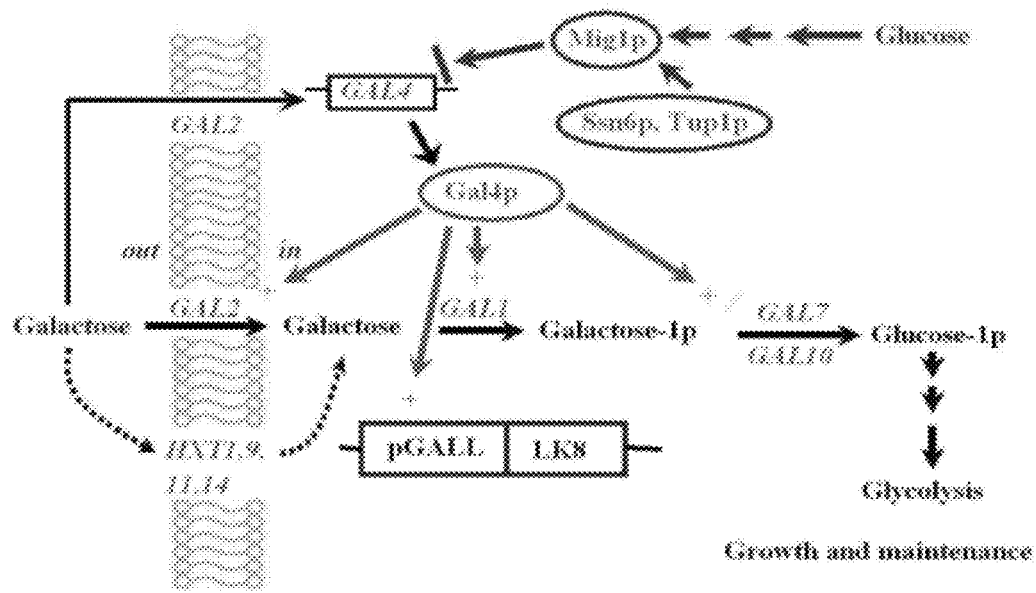
FIG. 1 is a schematic diagram illustrating a process where galactose in the culture medium passes through a yeast cell membrane and acts on a foreign protein expression-inducing promoter and a process where catabolite repression by glucose occurs in cells.

Hereinafter, the present invention will be described in more details.

A method for improving secretion efficiency of a foreign protein in accordance with the present invention comprises the steps of (a) transforming a yeast host with a recombinant foreign gene construct comprising a galactose-inducible promoter, a secretion signal sequence and a gene encoding the foreign protein to construct a transformed yeast strain; and (b) culturing the transformed yeast strain under the condition that the activity of the galactose-inducible promoter is controlled.

Herein, the step (a) is carried out to transform a yeast host with a recombinant foreign gene expression construct. There is no particular limitation to the trans-formation method. Preferably, transformation is carried out by insertion (or multiple insertion) of the recombinant foreign gene construct into the chromosome of the yeast host or by insertion of the gene construct into a cytoplasm of the yeast host such that it can be present in the form of a circular vector. Incorporation of the gene construct into the chromosome is called "integration" in transformation using yeast, whereas incorporation of the gene construct in the form of a circular vector into the yeast cytoplasm refers to episomal expression method in which a foreign gene is introduced in the form of episome to express and secrete the foreign protein after insertion of the foreign gene expression construct into a vector (or a plasmid) that is applicable to a yeast system. Episome is a circular DNA present in the cytoplasm and is capable of performing genetic functions independently of chromosomes of host cells.

Examples of the galactose-inducible promoter that can be used in the present invention may include any kind of promoter without particular limitation, so long as it is functionally operable in the yeast system by using galactose as an inducer. Preferably, there may be used a GAL1 promoter of S. cerevisiae set forth in SEQ ID NO: 1, a GAL10 promoter of S. cerevisiae set forth in SEQ ID NO: 2, a GAL7 promoter of S. cerevisiae set forth in SEQ ID NO: 3, or a combination or fusion thereof. More preferred is GAL1.

The secretion signal sequence may be any sequence that is used as the secretion signal in the yeast system or is conventionally known in the art. For example, the signal sequence may be selected from the group consisting of an MATα signal set forth in SEQ ID NO: 4, a K1 killer toxin signal of S. cerevisiae set forth in SEQ ID NO: 5 (Brown, J. L. et al., The K1 killer toxin: molecular and genetic applications to secretion and cell surface assembly. In: Johnston, J. R. Molecular Genetics of Yeast—a practical approach. The practical approach series, 1994, p. 217-265; and Tokunaga, M. et al., Biochem. Res. Commun., 144: 613-619, 1987), an invertase signal of S. cerevisiae set forth in SEQ ID NO: 6 (Japanese Unexamined Patent Publication No. 1985-041488), a killer toxin signal of Kluyveromyces lactis set forth in SEQ ID NO: 7 (Sugisaki, Y. et al., Eur. J. Biochem., 141: 241-245, 1984), a killer toxin signal of Pichia acaciae set forth in SEQ ID NO: 8 (U.S. Pat. No. 6,107,057), a killer toxin signal of Hanseniaspora uvarum (Radler, F. et al., Arch. Microbiol., 154(2): 175-178, 1990; and Schmitt, M. J. et al., J. Virol., 68(3):1765-1772, 1994), a killer toxin signal of Pichia (Hansenular) anomala, and any combination thereof.

Further, in order to enhance the secretion efficiency of proteins or peptides, the secretion signal sequence may further include a propeptide sequence, still further a recognition site of a signal peptidase such as KEX1 (for killer expression 1) or KEX2 (U.S. Pat. No. 4,929,553). An example of the recognition site of the signal peptidase may include Pro-Met-Tyr.

Meanwhile, the condition where the activity of the galactose-inducible promoter is controlled may be established using various methods such as genetic engineering techniques and culture techniques. There is no particular limitation to such techniques for establishment of desired culture conditions, so long as it is possible to control the activity of the galactose-inducible promoter. Preferably, the activity of the galactose-inducible promoter may be controlled by decreasing a transport rate of galactose from the culture medium into the transformed yeast strain.

In this connection, any method including genetic engineering-based strain modification techniques and culture techniques may be used to reduce an intracellular transport rate of galactose, so long as it is possible to reduce delivery of galactose into the cells. For example, various genetic engineering techniques may be used to make a galactose permease gene of the transformed yeast, as a target, non-functional. Preferably, it is preferred to decrease the transport rate of galactose by making the galactose permease gene defective or partially disrupting it to thereby be non-functional.

There is no particular limitation to methods for deficiency induction or disruption of the gene, so long as they are intended for (partially or completely) nullifying functions of galactose permease. For example, deficiency (deletion) or partial (or complete) disruption of the gene may be made using various genetic engineering techniques conventionally known in the art.

In addition, the galactose permease-defective strain that can be used in the present invention is not particularly limited. For example, *Saccharomyces cerevisiae* BJ3501 (ATCC 208280) is typically known.

Preferably, the condition for modulation of the galactose-inducible promoter activity in the step (b) is co-feeding of galactose and glucose in a certain ratio to the culture broth during culturing of cells. There is no particular limitation to culture methods including a batch culture, a continuous culture, a fed-batch culture and the like. Preferred is the fed-batch culture.

Further, there is no particular limitation to the ratio of galactose and glucose, so long as glucose catabolite repression brings about inhibition of intracellular transport of galactose while the induction by galactose is not inhibited. Preferably, the ratio of galactose and glucose is in a range of 4:1 to 1:1.

In the construction of the transformed yeast strain by transformation of a yeast host with a recombinant foreign gene construct comprising a galactose-inducible promoter, a secretion signal sequence and a gene encoding a foreign protein, the yeast host is preferably transformed with a recombinant foreign gene construct containing a protein disulfide isomerase-encoding gene that is expressed under the control of the galactose-inducible promoter.

Preferably, the method for improving secretion efficiency of a foreign protein further comprises, between the steps (a) and (b), a step (a-1) of further transforming the transformed yeast strain of the step (a) with a recombinant foreign gene construct containing a protein disulfide isomerase-encoding gene that is expressed under the control of the galactose-inducible promoter.

The aforementioned additional step (a-1) refers to re-transformation of the yeast strain with the gene encoding protein disulfide isomerase that exerts excellent effects on extracellular secretion of the proteins produced within cells.

The transformation of the yeast strain with the protein disulfide isomerase-encoding gene can be carried out by previous transformation of a yeast strain with the protein disulfide isomerase-encoding gene prior to the step (a) of constructing a transformed yeast via transformation of the yeast host with a recombinant foreign gene construct comprising a galactose-inducible promoter, a secretion signal sequence and a gene encoding a foreign protein, or otherwise by additional transformation step (a-1) of the transformed yeast strain with the protein disulfide isomerase-encoding gene after the step (a).

The protein disulfide isomerase-encoding genes that can be used in the present invention are not particularly limited to certain species-derived specific sequences, so long as they can perform disulfide isomerization. Preferably, the protein disulfide isomerase gene is selected from the group consisting of PDI1 of *S. cerevisiae* set forth in SEQ ID NO: 9 (Tachikawa, H. et al., J. Biochem., 110(2): 306-313, 1991), PDI of Conus textile set forth in SEQ ID NO: 10 (US Patent Application No. US2004/0203132 A1), PDI of *C. elegans* set forth in SEQ ID NO: 11 (Page, A. P., DNA Cell Biol., 16(11): 1335-1343, 1997), a human pancreatic PDI gene set forth in SEQ ID NO: 12 (Desilva, M. G. et al., DNA Cell Biol., 15(1): 9-16, 1997), PDI of *Aspergillus oryzae* set forth in SEQ ID NO: 13 (WO 95/00636), PDI of *Candida boidinii* set forth in SEQ ID NO: 14 (U.S. Pat. No. 5,965,426), PDI of *Humicola insolens* set forth in SEQ ID NO: 15 (U.S. Pat. No. 5,700,659) and any combination thereof.

The gene construct encoding protein disulfide isomerase is not particularly limited to specific vectors or equivalents thereof. Preferred is pMPDI having restriction sites illustrated in FIG. 8.

In the yeast expression system, the galactose-inducible promoter is widely used which has strong expression intensity. The galactose-inducible promoter is activated in the intracellular presence of galactose as an inducer, and then leads to abundant expression of a gene that is under the control of the above galactose-inducible promoter. Due to such inducibility, the galactose-inducible promoter is employed as a useful means in the expression of foreign recombinant proteins in yeast.

Figure 4:
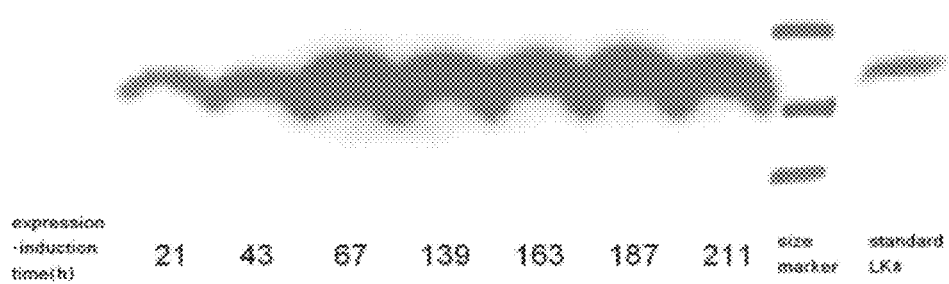
FIG. 4 is a photograph showing results of Western blot analysis for intracellular total foreign proteins with an expression-induction period, upon expression of a foreign gene in transformed yeast strain A.

However, as discussed before, the present inventors observed that insoluble precipitation of foreign proteins takes place in cells at the early stage of expression before secretion of the foreign proteins occurs (see FIG. 4).

The present inventors have conducted a variety of extensive and intensive studies and experiments to solve the aforementioned problems and to improve extracellular secretion of the foreign proteins. For this purpose, based on the fact that overactivation of the galactose-inducible promoter due to overabundance of galactose in the cells is primarily responsible for the intracellular insoluble precipitation of the foreign proteins before secretion thereof, the present inventors investigated to confirm whether the secretion efficiency of recombinant foreign proteins is improved by controlling intracellular influx of galactose that is used as an expression inducer of the galactose-inducible promoter.

First, upon analysis of an intracellular uptake route of galactose, intracellular transport of galactose may occur via various routes. The primary route of galactose transport is galactose permease (Gal2) which, as a constituent of the galactose operon, is expressed in the presence of galactose and exhibits the highest affinity for galactose.

However, even when a host cell is defective in galactose permease (Gal2) activity, galactose transport is not completely blocked. Instead, such a Gal2-defective host cell can achieve intracellular transport of galactose by additional methods, for example through various kinds of hexose transporters present on the cell membrane, such as HXT1, HXT9, HXT11, and HXT14 (Wieczorke R. et al., FEBS. Lett. 464 (3): 123-128, 1999), even though other hexose transporters have a relatively low affinity for galactose. So at least a minimum amount of galactose necessary for operation of a GAL promoter can be transported into the cell (see FIG. 1). FIG. 1 is a conceptual diagram illustrating a process where galactose in the culture medium passes through a yeast cell membrane and then acts on a promoter that induces expression of the foreign protein and a process where glucose causes catabolite repression in cells.

Based on this scheme shown in FIG. 1, the present inventors contemplated that it may be possible to minimize intracellular transport of galactose by using a yeast host which is defective in a gene (Gal2) coding for Gal2, a major transporter of galactose. For this purpose, first, a recombinant foreign gene construct, which expresses a foreign gene under the control of the galactose-inducible promoter, is introduced into *Saccharomyces cerevisiae* BJ3501 (ATCC 208280) with defects in a Gal2 gene (hereinafter, referred to as "yeast host B") as a host to thereby construct a transformed yeast (hereinafter, referred to as "transformed yeast strain B"), and the thus-transformed yeast strain was cultured in a galactose-containing medium. Thereafter, secretion efficiency of the recombinant foreign protein in the transformed yeast strain B was compared with that of another transformed yeast strain (hereinafter, referred to as "transformed yeast strain A") which was obtained by transformation of normal yeast strain (*Saccharomyces cerevisiae* 2805, hereinafter, referred to as "yeast host A") with no defects in the Gal2 gene as a host.

Figure 3:
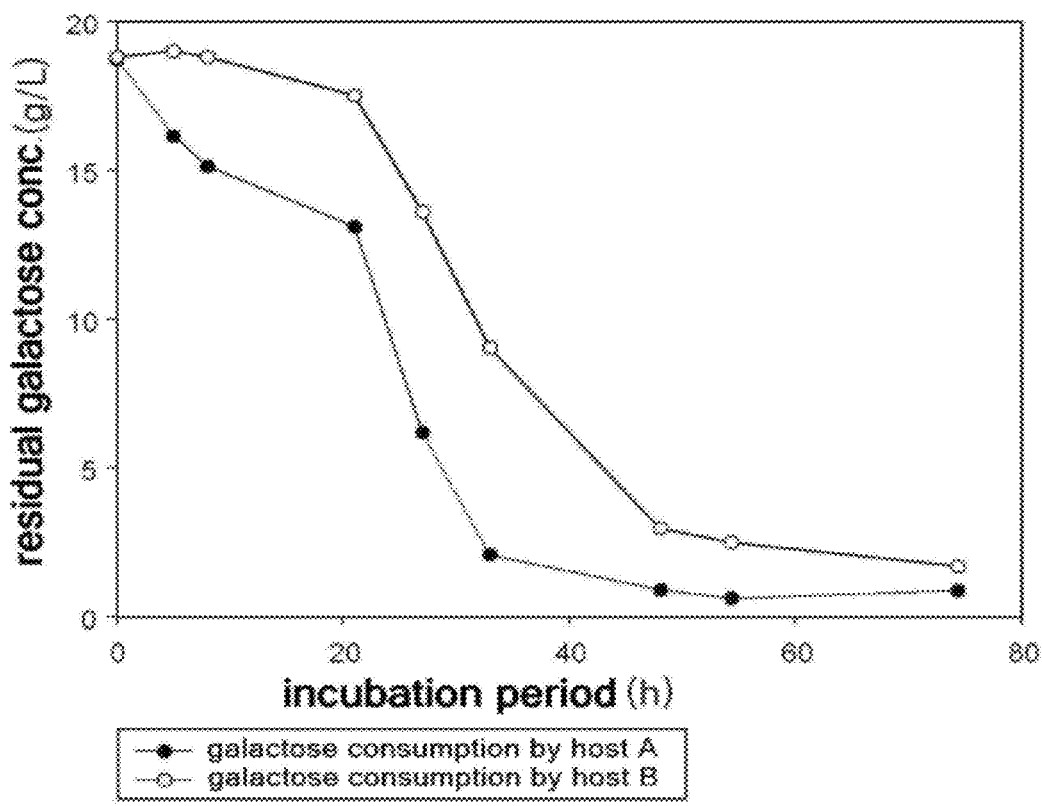
FIG. 3 is a graph comparing a galactose consumption rate over time, when two yeast hosts, each having the same genetic background with exception of a Gal2 gene, were cultured with a supply of galactose as a sole carbon source.

As shown in FIG. 3, when yeast hosts A and B, each having the same genetic background with exception of the Gal2 gene, were cultured in the media containing galactose as a sole carbon source, and concentrations of galactose over time in the culture media were determined and compared between two groups, it was confirmed that the influx rate of galactose into the cells significantly varies depending upon the presence/absence of Gal2 gene.

Figure 5:
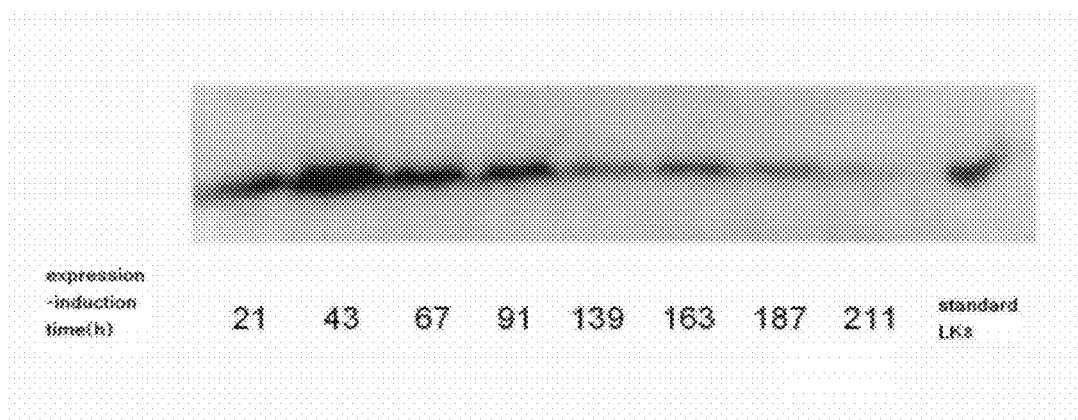
FIG. 5 is a photograph showing results of Western blot analysis for intracellular water-soluble foreign proteins in transformed yeast strain A.

Furthermore, it was confirmed through Western blot analysis using antibodies for foreign protein that intracellular insoluble precipitation of the foreign protein arising from overexpression of the foreign protein under the control of the galactose-inducible promoter was relatively decreased when yeast host B having a low influx rate of galactose into the cell due to non-operation of the Gal2 gene was employed as a host for expression of the foreign protein (see FIG. 6), as compared to when yeast host A was employed as the host for expression of the foreign protein (see FIGS. 4 and 5). In addition, it was also confirmed through HPLC analysis of the foreign protein secreted into the culture medium that increases in extracellular secretion and secretion efficiency of the foreign protein, the ultimate objects of the present invention, were also achieved in conjunction with the decreased insoluble precipitation of the foreign protein under practical culture conditions (see FIG. 7). In one embodiment of the present invention, even though a yeast strain with deletion of the galactose permease gene was used to decrease the intracellular influx of galactose, antisenses, siRNAs, antibodies, antagonists and the like, which suppress functions of the galactose permease gene, may also be used for the same purpose.

For appropriate regulation of intracellular availability of galactose, the present inventors have adopted a strategy in which glucose causing catabolite repression (repression of expression of certain sugar-metabolizing genes in favor of glucose utilization when glucose is the predominant carbon source in the culture medium environment of the cell) and galactose serving as the inducer of the galactose-inducible promoter were "co-fed" into a fed-batch medium to induce simultaneous consumption of two sugars such that overexpression of the foreign protein is appropriately regulated by catabolite repression depending upon a proportion of glucose included in the culture medium.

FIG. 1 is a schematic diagram illustrating two contrary actions of galactose and glucose on induction and repression of the galactose-inducible promoter in the cell (K.-D. Entian and H.-J. Schuller, Glucose Repression in Yeast. In: Yeast Sugar Metabolism, F. K. Zimmermann, K.-D. Entian., eds. pp. 409-434. Technomic Publishing AG, Bassel, Switzerland, 1997).

In this connection, complete repression of the galactose-inducible promoter by glucose was prevented by feeding a mixed carbon source via a glucose-limited fed-batch culture adapted to maintain a glucose concentration of less than 0.1 g/L in the culture medium.

The present inventors named the above-mentioned method as a mixed-carbon source feeding strategy. In the present invention, cells were cultured in the fed-batch media containing varying ratios of glucose/galactose, and secretion of the foreign protein was artificially controlled for each case. In addition, amounts of the secreted foreign protein at different ratios of glucose/galactose were compared to thereby confirm an optimum glucose/galactose ratio necessary for secretion of the foreign protein in yeast host strains having different galactose transport capacities (see Tables 1 and 2 below).

When the mixed-carbon source feeding method designed by the present invention was applied to yeast hosts A and B, production yield of the foreign protein per cell and production yield of the foreign protein per inducer increased by 105% (Table 1) and by 85% (Table 2), respectively, as compared to a conventional expression induction method using only galactose as a sole carbon source. Further, when the aforementioned transformed yeast strains A and B were respectively fed-batch cultured by application of the mixed-carbon source feeding method, it was revealed that there are different optimum glucose/galactose concentrations.

The transformed yeast strain A having a relatively high intracellular influx and consumption rate of galactose exhibited an about 1:1 glucose/galactose ratio of the mixed carbon source for optimum secretion of the foreign protein, whereas the transformed yeast strain B having a decreased galactose transport capacity due to non-operation of galactose permease exhibited an about 2:3 optimum ratio of the mixed carbon source (glucose/galactose), thus requiring a relatively high proportion of galactose in the medium, as compared to the transformed yeast strain A (see Tables 1 and 2). These results indirectly demonstrate that effects of the galactose transport capacity and mixed carbon source on expression of the foreign protein in the foreign protein-expression system using the galactose-inducible promoter are consistent well with the intention of the present invention.

On the other hand, the present inventors investigated to confirm whether the protein secretion efficiency is improved by transformation of a host cell with a gene (PDI1) coding for protein disulfide isomerase known as a protein folding assistant, in conjunction with a foreign gene construct that is expressed under the control of the galactose-inducible promoter.

First, an expression vector pMPDI1 containing the protein disulfide isomerase gene (PDI1) of *S. cerevisiae* set forth in SEQ ID NO: 9 was constructed, and the resulting expression vector in conjunction with the foreign gene construct were transformed into yeast host strains A and B, respectively. Then, the transformed yeast strains were cultured in a galactose-containing medium, and the protein secretion efficiency was determined (see Table 3). As a result, it can be seen that transformation of yeast host A with the foreign gene construct and the pMPDI1 vector exhibited a 30% increase in the protein secretion efficiency relative to a control group (yeast host A having no incorporation of PDI1 gene), whereas transformation using yeast host B exhibited a 72% increase in the protein secretion efficiency relative to the control group.

As reviewed above in detail, the method of improving secretion efficiency of a foreign protein in accordance with the present invention enables improvements in the secretion efficiency of a recombinant foreign protein by decreasing overexpression-induced insoluble precipitation of foreign proteins encountered in conventional galactose-inducible promoter-based yeast expression systems, via moderate control of a level of galactose functioning as an inducer of the galactose-inducible promoter in cells. Therefore, the method of the present invention can be usefully employed to improve the productivity of recombinant foreign proteins in the yeast expression system and lower the production costs.

MODE FOR THE INVENTION

Examples

Now, the present invention will be described in more detail with reference to the following examples. These examples are provided only for illustrating the present invention and should not be construed as limiting the scope and spirit of the present invention.

Example 1

Comparison of Intracellular Galactose Transport Capacity Between Yeast Hosts A and B Yeast host A (*S. cerevisiae* 2805, Genotype: MATα pep4::HIS3 prbl-Δ1.6R his 3-Δ200 ura3-52 GAL2 can1, Sohn, J. H. et al. Proc. Biochem., 30: 653-660, 1995; and Kim, T. H. et al. Biotechnol. Lett. 24: 279-286, 2002) and yeast host B (*S. cerevisiae* BJ3501, Genotype: MATα pep4::HIS3 prb1-Δ1.6R his3-Δ200 ura3-52 gal2 canl, ATCC 208280, USA) were streaked on YPD agar plates and placed in an incubator at 30° C. for about 18 hours, and colonies were isolated. Each colony of yeast strains A and B was inoculated into separate YPG [yeast extract 1% (w/v), peptone 2% (w/v), and galactose 2% (w/v)] liquid media and shake-cultured in an incubator at 30° C. for about 80 hours. In order to determine galactose consumption over time, a residual galactose concentration in the medium was determined by quantification of reducing sugar via 3,5-dinitrosalicylic acid (DNS) assay (Mohun, A. F. and Cook, I. J., J. Clin. Pathol., 15: 169-180, 1962, see FIG. 3).

FIG. 3 is a graph comparing a galactose consumption rate over time, when two yeast hosts, each having the same genetic background with exception of defects in a Gal2 gene, were cultured with a supply of galactose as a sole carbon source. As can be seen in FIG. 3, it was confirmed that Gal2 gene-defective yeast host B exhibited decreases in a consumption rate of galactose per unit time, as compared to yeast host A where the Gal2 gene normally functions.

Example 2

Construction of Yeast Transformants Secreting Foreign Proteins, Using Yeast Hosts A and B 2-1. Construction of Yeast Transformant *S. cerevisiae* 2805/MδLK8 Secreting Foreign Proteins, Using Yeast Host A Co-isolation of an α-factor secretion signal and a LK8 cDNA was carried out using an expression vector pMBR1-LK8 (Korean Patent Publication Laid-open No. 2004-0069840) which was used to produce recombinant LK8 in *Pichia pastoris* by the present inventors. This application is incorporated by reference herein in its entirety. The pMBR1-LK8 vector was treated with EcoR I for 7 hours, and was washed using a PCR Purification Kit (Qiagen, USA). Then, the vector was treated with BamH I for 7 hours, and DNA was isolated by gel electrophoresis. Using a gel extraction kit (Qiagen, USA), a DNA fragment was obtained which has an α-factor secretion signal of SEQ ID NO: 4 and an LK8 cDNA sequence of SEQ ID NO: 16. The thus-obtained DNA fragment was inserted between a GAL1 promoter and a CYC1 terminator of a p426GAL1 (ATCC 87833, USA) vector to thereby construct an expression vector pMCLK8 (6.9 kb) that can be used to produce recombinant LK8 in yeast. The resulting vector pMCLK8 contains the GAL1 promoter which thus allows induction of protein expression by galactose. Following transformation of yeast, transformants were selected in a selection medium using a URA3 marker as a selection marker. Thereafter, in order to insert an expression cassette consisting of the α-factor secretion signal sequence and the LK8 cDNA into a chromosome of yeast, the expression cassette was inserted into a pδneo vector (Lee, F. W. and Da Silva, N. A., Appl. Microbiol. Biotechnol., 48:339, 1997) containing a δ sequence and a neomycin resistance gene (neo) for selection of the inserted vector as follows, so as to ensure that a desired gene can be inserted into the δ sequence, one of transposable elements located in yeast chromosome.

Figure 2:
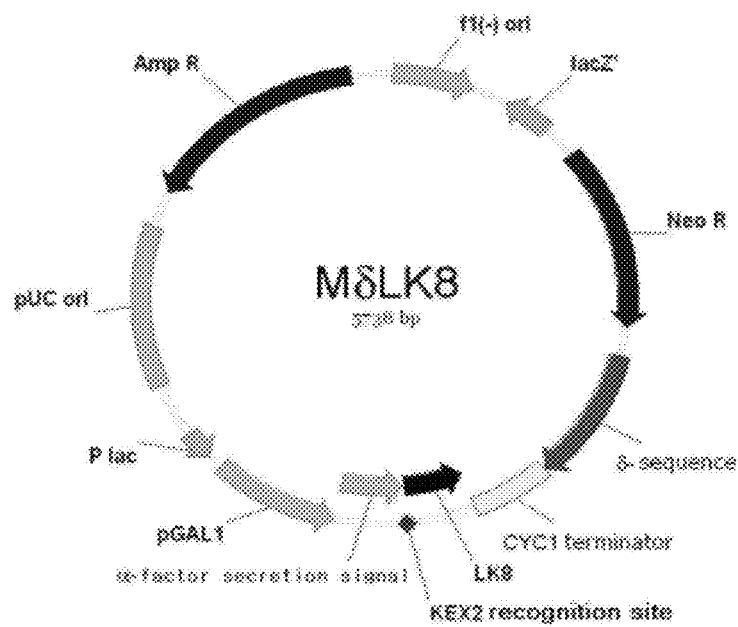
FIG. 2 is a cleavage map of a recombinant LK8 protein expression vector MδLK8 used in the present invention.

First, the LK8 expression cassette was separated from the pMCLK8 vector, using restriction enzymes Sac I and Kpn I which cleave both ends of the GAL1 promoter and CYC1 terminator, respectively. Herein, since both sequences of the LK8 expression cassette and the pδneo vector contain Sal I restriction sites and the Sal I restriction site present on the pδneo vector is essentially required for incorporation of the vector into the yeast chromosome, a DNA blunting kit (Takara, Japan) was employed to remove the Sal I restriction site present on the LK8 expression cassette. On the other hand, because the pδneo vector contains no Kpn I restriction site, the above-mentioned DNA blunting kit was used to convert both an Xba I restriction site of the pδneo vector and a Kpn I restriction site of the separated LK8 expression cassette to blunt ends. Then, the thus-blunted LK8 expression cassette and the pδneo vector were ligated with ligase to construct a recombinant vector, which was designated an MδLK8 recombinant expression vector (FIG. 2). FIG. 2 is a cleavage map of a recombinant LK8 protein expression vector MδLK8 which was used in the present invention.

Thereafter, *Saccharomyces cerevisiae* 2805 (Sohn, J. H. et al. Proc. Biochem., 30: 653-660, 1995; and Kim, T. H. et al., Biotechnol. Lett., 24: 279-286, 2002) was transformed with the above recombinant MδLK8 expression vector using Alkali Cation Yeast Transformation Kit (Q-BIOgene, Canada). The yeast strains transformed with the MδLK8 recombinant expression vector were selected using a YPD plate containing antibiotic G418 sulfate [2% (w/v) peptone, 1% (w/v) yeast extract, 2% (w/v) glucose and 2% (w/v) agar]. A concentration of G418 sulfate was adjusted to 5 g/L, 10 g/L and 15 g/L, respectively, to thereby select the highest antibiotic-resistant yeast strain, which was designated *Saccharomyces cerevisiae* 2805/MδLK8. Hereinafter, this yeast strain will be referred to as "transformed yeast A" for the sake of brevity and convenience.

2-2: Construction of Yeast Transformant *S. cerevisiae* BJ3501/MδLK8 Secreting Foreign Proteins, Using Yeast Host B According to the same manner as in Example 2-1, *Saccharomyces cerevisiae* BJ3501 (ATCC 208280, USA), having the same genotype with exception of defects in a GAL2 gene as *Saccharomyces cerevisiae* 2805, was transformed with the recombinant expression vector MδLK8 constructed in Example 2-1. Then, colony screening was carried out to select a clone having the highest secretion efficiency which was finally designated *Saccharomyces cerevisiae* BJ3501/MδLK8 #36 and deposited with the Korean Collection for Type Cultures (KCTC), Korea Research Institute of Bioscience and Biotechnology (KRIBB, Daejon, Korea), under Accession Number KCTC 10582BP (deposited on Jan. 13, 2004). Hereinafter, this transformant strain will be referred to as "transformed yeast strain B" for the sake of brevity and convenience.

Example 3

Comparison of Foreign Protein-Secretion Capacity Between Transformed Yeast Strains A and B in Fed-Batch Culture Using Galactose as Carbon Source Where yeast transformants A and B constructed in Example 2 were fed-batch cultured using galactose, the following analysis was performed to compare the secretion efficiency of foreign proteins. First, the transformed yeast strains as master seeds were seed-cultured in a YPD [yeast extract 1% (w/v), and peptone 2% (w/v)] medium supplemented with 2% (w/v) glucose at 1 to 3 vvm air and 200 to 1000 rpm for 24 hours, such that desired cell mass and activity (20-fold diluted, OD600=0.8 to 1.2) can be obtained. After seed culture was carried out in the YPD medium, the seed culture solution was inoculated into a starting medium. First, a batch-culture stage is a cell growth period and an adaptation period to galactose that is used as an expression inducer of foreign protein LK8. For this purpose, cells were given a galactose-adaptation period while allowing multiplication of cells by inoculating more than 1% (v/v) seed culture solution and supplying glucose and galactose as a carbon source. Herein, the starting medium was composed of 2% (w/v) glucose, 3% (w/v) galactose, 4% (w/v) yeast extract, 0.5% (w/v) casamino acid, 0.5 g/L of uracil and 0.5 g/L of histidine.

Upon depletion of the carbon source supplied to the starting medium at the batch culture stage, respiratory action (oxygen consumption) of cells is lowered, which can be confirmed from a sharp increase in the dissolved oxygen level by a dissolved oxygen probe provided on a fermenter. From this time point, a fed-batch culture was carried out with an addition of a medium containing galactose as a sole carbon source, using a DO-stat feeding strategy. The fed-batch culture was carried out to further increase a cell concentration and further continuously maintain an expression induction period of the foreign proteins, thereby improving the productivity of the foreign protein.

Specifically, a fed-batch medium composed of 50% (w/v) galactose, 30 g/L of yeast extract, 20 g/L of peptone, 1 g/L of uracil and 2 g/L of histidine was used (fed-batch medium 1). In order to induce high-level secretion of the foreign protein LK8, an amount of residual galactose in the culture medium was maintained below 5% (w/v) by feeding galactose at a rate of 1 mL/hr to 30 mL/hr. Galactose feeding was carried out by determining a residual concentration of galactose in the culture medium and adding a suitable amount of galactose based on the thus-obtained value to thereby maintain a level of residual galactose at an appropriate value. Expression and secretion of LK8 could be augmented continuously while maintaining the concentration of residual galactose in a fermenter throughout a fermentation period below 5% (w/v) by controlling an addition rate of galactose.

The fed-batch culture method was applied to transformed yeast strains A and B constructed in Example 2 under the same culture conditions, and expression and secretion profiles of the foreign protein with respect to galactose transport capacity of yeast were compared between two yeast groups. First, in order to compare distribution profiles of the foreign protein accumulated in the yeast cells, Western blot analysis using anti-LK8 antibodies was carried out on culture samples collected from both yeast groups at given time points of an incubation period. For this purpose, each transformed yeast strain collected periodically during the incubation period was adjusted to the same amount, boiled in an equal volume of a sample buffer and electrophoresed on SDS-polyacrylamide gel to develop intracellular proteins. The thus-developed proteins were transferred to nitrocellulose membranes. For blotting, the nitrocellulose membranes were put in solutions supplemented with a PBS buffer solution containing 0.1% (v/v) Tween 20® and 5% (w/v) skimmed milk, which were gently stirred at room temperature for 2 hours. Thereafter, rabbit anti-LK8 Abs were added to the same solution which was then gently stirred at room temperature for 1 hour and repeatedly washed five times with PBS buffer containing 0.1% (v/v) Tween 20®. Next, anti-rabbit IgG-HRP (anti-rabbit IgG-horseradish peroxidase, Sigma, USA) was added to solutions supplemented with a PBS buffer solution containing 0.1% (v/v) Tween 20® and 5% (w/v) skimmed milk, and the thus-treated nitrocellulose membranes were dipped in the solutions to which anti-rabbit IgG-HRP was added and gently stirred at room temperature for 1 hour. Then, the membranes were repeatedly washed five times with PBS buffer solution containing 0.1% (v/v) Tween 20®. The membranes were taken out and were induced to undergo luminous reaction in a chemiluminescence detection kit (SuperSignal™ West Pico kit, Pierce, USA) with an addition of a detection solution, and fixed on photosensitive films. Shading on the film was examined (see FIGS. 4, 5 and 6). FIG. 4 is a photograph showing results of Western blot analysis for intracellular total foreign proteins with an expression-induction period, upon expression of a foreign gene in transformed yeast strain A; FIG. 5 is a photograph showing results of Western blot analysis for intracellular water-soluble foreign proteins in transformed yeast strain A; and FIG. 6 is a photograph showing results of Western blot analysis for total intracellular foreign proteins with an expression-induction period, upon expression of a foreign gene in transformed yeast strain B.

As shown in FIG. 4, it can be seen that continuation of fed-batch culture inducing expression of the foreign gene leads to higher intracellular accumulation of the foreign proteins, when galactose transport capacity is normal due to normal operation of a GAL2 gene. However, as shown in FIG. 5, it can be seen that when Western blot analysis was performed only for water-soluble proteins in the cells, the foreign proteins were primarily in the form of insoluble proteins with respect to the passage of time, rather than in the form of soluble proteins. On the other hand, as shown in FIG. 6, it can be seen that transformed yeast strain B having decreased galactose transport capacity due to defects in the Gal2 gene exhibited decreases in the intracellular accumulation of the foreign proteins over the expression period.

Figure 6:
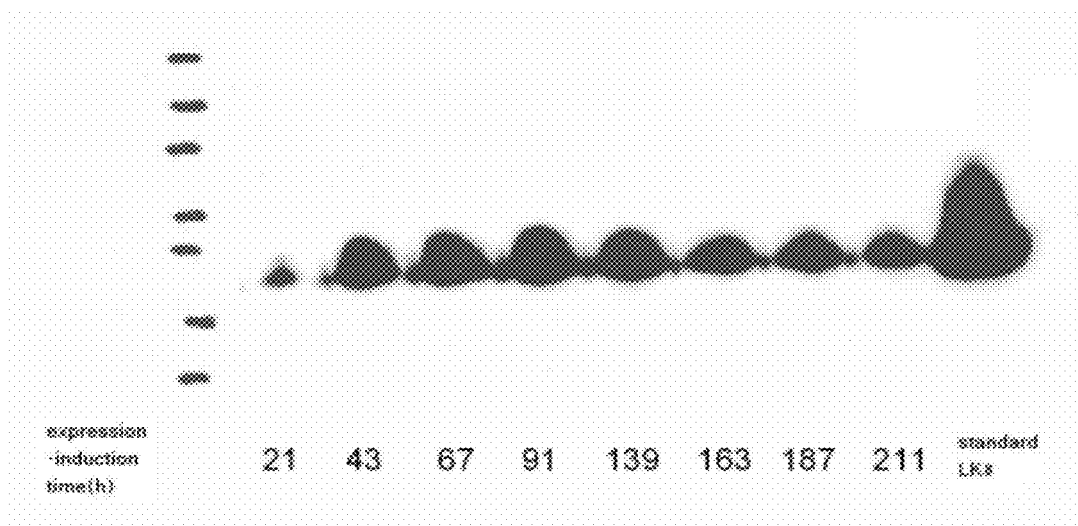
FIG. 6 is a photograph showing results of Western blot analysis for intracellular total foreign proteins with an expression-induction period, upon expression of a foreign gene in transformed yeast strain B. As can be seen, intracellular insoluble accumulation of the foreign proteins relatively decreases with time, as compared to protein expression using yeast strain A having a GAL2 gene as a host.

In order to confirm whether the results of FIG. 6 are due to improved secretion efficiency of the foreign protein in the transformed yeast strain B with defects in the GAL2 gene, or otherwise due to an overall decrease in the protein expression level, the transformed yeast strains A and B constructed in Example 2 were fed-batch cultured under the same culture conditions, and the cell cultures were subjected to high-performance liquid chromatography (HPLC) analysis to quantify the secreted foreign proteins. First, the cell culture was centrifuged and the resulting supernatant was filtered through a 0.2☐ filter. Then, 100☐ of the filtered sample was subjected to determination of absorbance (OD) at a wavelength of 214 nm in HPLC. The foreign protein LK8 was separated using a developing solvent, e.g. acetonitrile containing 1% (w/v) trifluoroacetic acid (TCA) and water containing 1% (w/v) TCA as a mobile phase by a reverse phase separation column (Vydac™ c18 column, Grace Vydac, USA). Herein, the mobile phase was composed of a gradient starting from 25% (v/v) to 40% (v/v) acetonitrile, thereby being capable of separating a pure foreign protein having a single peak taking advantage of hydrophobic interaction. Further, after the highpurity foreign protein as a standard was determined by the bicinchoninic acid (BCA) assay, area integration in HPLC and a calibration curve for a concentration of the foreign protein could be obtained. Using the thus-obtained calibration curve, the cell-free culture supernatant was subjected to HPLC analysis to thereby calculate an integral area and the obtained value was applied to the calibration curve using the standard sample (LK8) to thereby quantify the foreign protein in the culture supernatant (FIG. 7).

Figure 7:
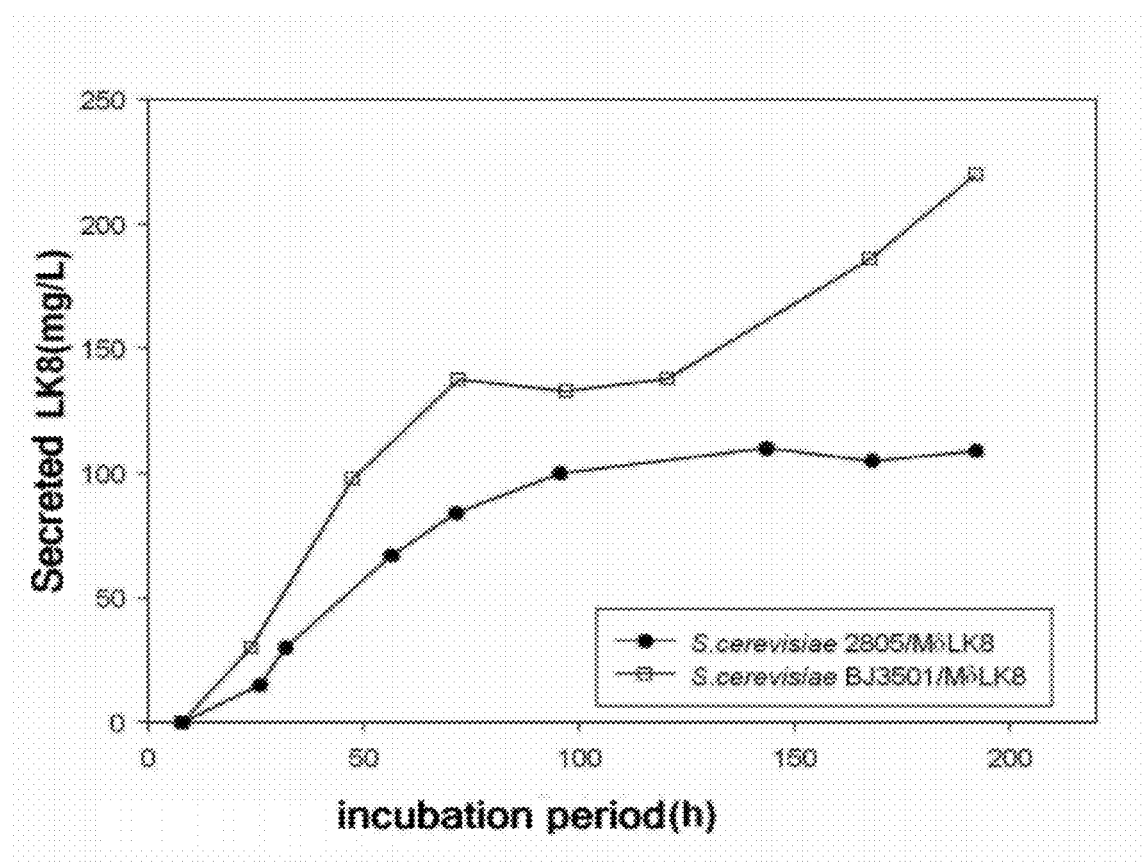
FIG. 7 is a graph comparing amounts of recombinant foreign proteins secreted into a culture medium versus an expression-induction period, upon expression of a foreign gene by fed-batch culture of transformed yeast strains A and B.

FIG. 7 is a graph comparing amounts of recombinant foreign proteins secreted into the culture medium over an expression induction period, upon expression of the foreign gene by fed-batch culture of transformed yeast strains A and B. In this graph, a filled circle (-●-) represents extracellular secretion of the recombinant foreign protein in transformed yeast strain A (*S. cerevisiae* 2805/MδLK8), whereas a open square (-□-) represents extracellular secretion of the recombinant foreign protein in transformed yeast strain B (*S. cerevisiae* BJ3501/MδLK8). As shown in FIG. 7, it can be seen that transformed yeast strain B with a decreased galactose transport exhibited a more than 2-fold increase in extracellular secretion of the protein, as compared to that of transformed yeast strain A having normal galactose transport function.

Example 4

Effects of Mixed-Carbon Source Feeding on Repression of Activity of Galactose-Inducible Promoter in Transformed Yeast Strain A and Comparison of Secretion Yield of Foreign Proteins Transformed yeast strain A of Example 2-1 under storage at −70° C. was inoculated at a concentration of 5 to 10% (v/v) onto 10 mL of a YPD medium, and seed-cultured in a shaking incubator at 30° C. and 180 rpm for 24 hours (first seed-culture stage). Then, the cultured cells were passaged in 200 mL of an YPD medium and seed-cultured for 24 hours under the same culture conditions (second seed-culture stage). Batch culture was carried out in a culture medium composed of 4% (w/v) yeast extract, 3% (w/v) casamino acid, 0.05% (w/v) histidine, 0.05% (w/v) uracil, 2% (w/v) glucose and 3% (w/v) galactose, while adjusting the culture conditions to 30° C., 600 rpm, and pH 5.0, respectively. Control of the batch culture was made by varying speed of a stirrer depending upon an amount of dissolved oxygen. In the late stage of batch-culture, dissolved oxygen is decreased because of vigorous respiration of cells. In order to prevent the decrease of dissolved oxygen, air supply and stirring speed were controlled to keep dissolved oxygen above 40% of maximum dissolved oxygen, until batch-culture is completed. Thereafter, fed-batch-culture was carried out in a culture medium composed of 3% (w/v) yeast extract (Difco, USA), 2% (w/v) peptone (Difco, USA), 0.2% (w/v) histidine (Sigma, USA), and 0.1% (w/v) uracil (Sigma, USA). As a control group, a concentration of galactose was adjusted to 50% (w/v). For an experimental group with a 1:4 ratio of glucose and galactose, glucose and galactose were added to concentrations of 10% (w/v) glucose and 40% (w/v) galactose, respectively. For an experimental group with a 1:1 ratio of glucose and galactose, glucose and galactose were added to concentrations of 25% (w/v) glucose and 25% (w/v) galactose, respectively. For an experimental group with a 4:1 ratio of glucose and galactose, glucose and galactose were added to concentrations of 40% (w/v) glucose and 10% (w/v) galactose, respectively.

The fed-batch culture was carried out by controlling a supply rate of a liquid medium to ensure that dissolved oxygen is maintained at a 20 to 80% level of maximum dissolved oxygen, the concentration of the remaining total reducing sugars (galactose+glucose) in the medium is maintained at a level of 0.5 to 5% (w/v), and the glucose concentration is maintained at less than 0.1 g/L. During batch culture and fed-batch culture, samples were periodically collected, and determination of OD at 600 nm, determination of a carbon source and quantification of secreted foreign protein (LK8) were carried out (Table 1).

Determination of the carbon source was carried out by measuring the residual amount of glucose and galactose in the medium. First, determination of the glucose concentration was carried out by an enzymatic method using a glucose assay kit (Glucose-E Kit, cat # BC103-E, Young-Dong Pharm., Seoul, Korea) as follows. The collected sample was centrifuged at 12,000 rpm and the resultant supernatant was taken. 100 mL of diluted powder of PGO enzyme (peroxidase 100 U+glucose oxidase 500 U) contained in the above assay kit using the enzymatic method and 100 mL of buffer were mixed to prepare a coloring reagent. 20□ of a glucose standard sample was added to 3 mL of the coloring reagent. According to the same method as described above, 20□ of an assay sample was also added to the coloring reagent. The resulting mixtures were reacted at 37° C. for 5 min, and the absorbance (OD) for each sample was determined at a wavelength of 505 nm. The absorbance values for the glucose standard sample and the assay sample were applied to a given equation and amounts of the residual glucose in the medium were calculated. Total carbon source in the medium was determined by DNS (3,5-dinitrosalicylic acid) assay that measures the total reducing equivalent. Both of glucose and galactose are reducing sugars and exhibit the same responsiveness to the same equivalent of the DNS coloring reagent. 100□ of an assay sample was added to 1 mL of the DNS reagent to which 2 M sodium hydroxide, 0.25 g of 3,5-dinitrosalicylic acid, and 75 g of sodium potassium tartrate were added based on total 300 mL of the reagent. This was followed by boiling of the mixture for about 5 min and measurement of absorbance at 550 nm to determine the total carbon source remaining in the medium. Amounts of the foreign protein secreted into the culture medium were determined by HPLC analysis in the same manner as in Example 3.

TABLE 1

Production yield per cell and production yield per inducer, upon fed-batch culture of transformed yeast strain A with varying ratios of galactose and glucose

| Weight ratio of glucose:galactose in culture medium | Total galactose consumed (g) | LK8 secreted (mg/L) | Cell growth (OD$_{600}$) | Yp/i[1] (mg/g) | Yp/x[2] (mg/L/OD) |
|---|---|---|---|---|---|
| Control (galactose only) | 270 | 100 | 120 | 0.37 | 0.83 |
| 1:4 | 200 | 114 | 100 | 0.57 | 1.14 |
| 1:1 | 190 | 150 | 88 | 0.79 | 1.70 |
| 4:1 | 78 | 44 | 77 | 0.56 | 0.57 |

[1]Yp/i: production yield per inducer (inducer yield), Unit: amount of secreted foreign protein per expression inducer (galactose)
[2]Yp/x: Production yield per cell (product yield), Unit: amount of secreted foreign protein per cell Where fed-batch culture was carried out with only galactose as the carbon source and with varying ratios of galactose and glucose after completing batch culture, cell growth, consumption of the carbon source and secretion of the foreign protein were compared respectively.

As shown in Table 1, fed-batch culture using only galactose as a sole carbon source exhibited extracellular secretion of the foreign protein (LK8) in a concentration of up to about 100 mg/L, and showed the highest cell growth (OD600=120), as compared to other experimental groups.

When cells were fed-batch cultured with a 1:4 ratio of glucose and galactose, secretion of the foreign protein exhibited a level of up to 114 mg/L, and the secretion of the foreign protein per the added expression inducer (galactose) increased by 40%. The added glucose was completely consumed within 24 hours during which batch culture was carried out, and glucose added during fed-batch culture was also immediately consumed to keep a residual concentration of less than 0.1 g/L.

Upon fed-batch culture with a 1:1 ratio of glucose and galactose, the secretion of LK8 showed the highest value of up to about 150 mg/L, as compared to other experimental groups. Further, it was confirmed that extracellular secretion increased by 50%, and the production yield per cell (Yp/x: mg/L/OD600) and the production yield per inducer (Yp/i, mg/g) increased by 104% and by 114%, respectively, as compared to the control group, thereby confirming increases in the secretion efficiency of the foreign protein.

Upon fed-batch culture with a 4:1 ratio of glucose and galactose, expression and secretion of the foreign protein were inhibited due to a high proportion of glucose, thus exhibiting only a maximum secretion of about 44 mg/L.

Example 5

Effects of Mixed-Carbon Source Feeding on Repression of Activity of Galactose-Inducible Promoter in Transformed Yeast Strain B and Comparison of Secretion Yield of Foreign Proteins Except that transformed yeast strain B constructed in Example 2-2 was used as a strain, cell growth, consumption of a carbon source and secretion of a foreign protein were compared in the same manner as in Example 4, when fed-batch culture of yeast strain B was carried out with only galactose as the carbon source and with varying ratios of galactose and glucose, respectively (see Table 2).

TABLE 2

Production yield per cell and production yield per inducer, upon fed-batch culture of transformed yeast strain B with varying ratios of galactose and glucose

| Weight ratio of glucose:galactose in culture medium | Total galactose consumed (g) | LK8 secreted (mg/L) | Cell growth (OD$_{600}$) | Yp/i[1] (mg/g) | Yp/x[2] (mg/L/OD) |
|---|---|---|---|---|---|
| Control (galactose only) | 800 | 250 | 62 | 0.31 | 4.03 |
| 1:4 | 604 | 300 | 39 | 0.50 | 7.84 |
| 2:3 | 287 | 350 | 47 | 1.22 | 7.44 |
| 1:1 | 240 | 330 | 69 | 1.06 | 5.19 |
| 3:2 | 180 | 140 | 50 | 0.53 | 2.8 |

[1]Yp/i: production yield per inducer (inducer yield), Unit: amount of secreted foreign protein per expression inducer (galactose)
[2]Yp/x: Production yield per cell (product yield), Unit: amount of secreted foreign protein per cell As shown in Table 2, fed-batch culture using only galactose as a sole carbon source exhibited extracellular secretion of the foreign protein (LK8) in a concentration of about 250 mg/L.

When fed-batch culture was carried out with a 1:4 ratio of glucose and galactose, secretion of the foreign protein exhibited a level of up to 300 mg/L. In addition, glucose was completely consumed within 24 hours during which batch culture was carried out, and glucose added during fed-batch culture was also immediately consumed.

Upon fed-batch culture with a 2:3 ratio of glucose and galactose, maximum secretion of LK8 appeared at a time point of 160 hours and the absorbance reflecting the cell growth was OD600=47. In connection with accumulation of sugar, it was also confirmed that both of glucose and galactose were utilized as the carbon source. A maximum secretion amount of the foreign protein was about 350 mg/L, thus representing that the time to reach the maximum secretion amount is shortest, as compared to other experimental groups. Further, it was confirmed that secretion of the foreign protein increased by 40%, and the production yield per cell (Yp/x: mg/L/OD600) and the production yield per inducer (Yp/i, mg/g) increased by 293% and by 85%, respectively, as compared to the control group, thereby confirming remarkable increases in secretion efficiency of the foreign protein.

Upon fed-batch culture with a 1:1 ratio of glucose and galactose, the cell growth was most active, as compared to other experimental groups. Further, the secretion amount of LK8 showed a significantly high value of up to about 350 mg/L. However, upon comparing with the experiment using a 2:3 ratio of glucose and galactose, showing a similar maximum secretion amount, the experiment using a 1:1 glucose and galactose ratio took about 380 hours to reach the secretion amount of 350 mg/L, showing that an about 2.5-fold longer incubation period is required to reach the same maximum secretion level of the foreign protein.

Upon fed-batch culture with a 3:2 ratio of glucose and galactose, the cell growth was relatively high, and sugar consumption was also active. However, expression and secretion of the foreign protein were inhibited due to a high proportion of glucose, thus exhibiting only a maximum secretion of about 140 mg/L.

Example 6

Figure 8:
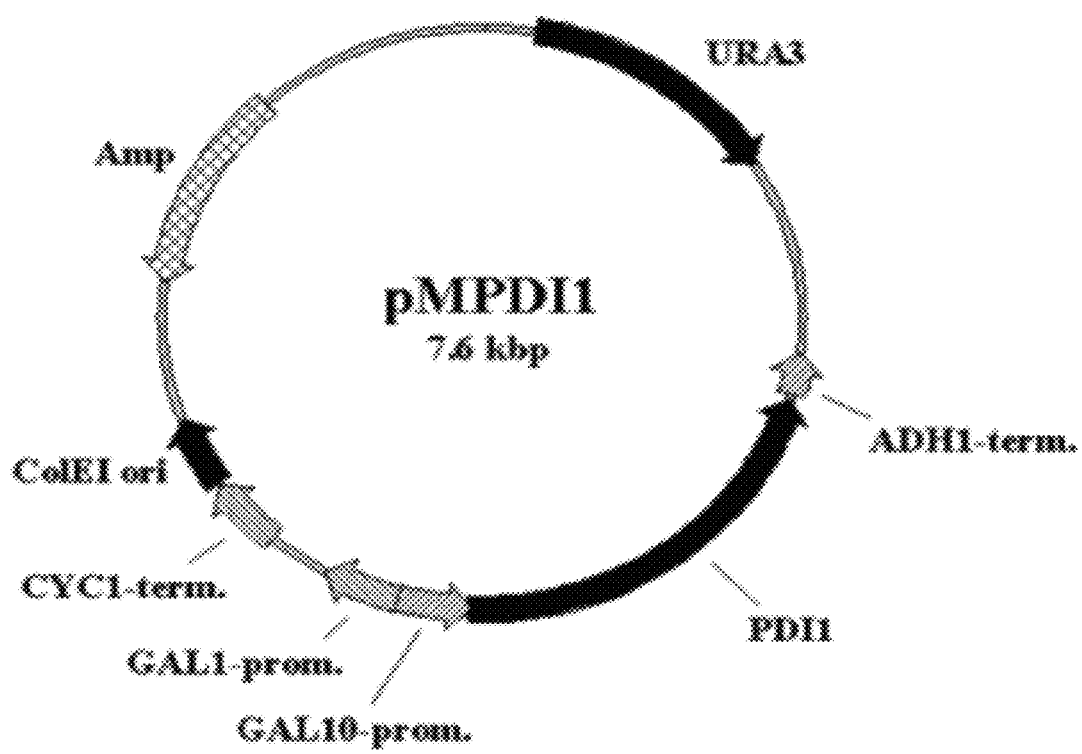
FIG. 8 schematically show restriction sites of an expression vector pMPDI1 adapted to allow co-expression of galactose-inducible protein disulfide isomerase gene (PDI 1), upon expression of a foreign protein in yeast.

Improvement in Secretion Efficiency of Foreign Protein Via Over-Expression of PDI1 Gene in Yeast Strains A and B 6-1. Construction of PDI1-Co-Expression Strain
6-1-1. Construction of PDI1 Expression Vector In order to ensure that protein disulfide isomerase (PDI) can be expressed by galactose induction, according to the following method a PDI1 gene encoding the protein disulfide isomerase was inserted into an expression vector containing a GAL10 promoter: first, in order to remove a 2µ, yeast replication origin, pESC-URA (Stratagene, USA) was cleaved with Mun I and SnaB I, and treated with DNA polymerase (Klenow fragment, New England Biolabs, USA), thereby resulting in religation of the resulting 5.9-kb blunt-ended DNA fragment to obtain an optimized vector pMK71. Using the resulting vector pMK71, S. cerevisiae 2805-derived chromosome as a template, and two primers PDI1F: 5'-ATAA-GAATGCGGCCGCCATACATCTATCCCGTTATGAAG-3' (SEQ ID NO: 17) and PDI1R: 5'-GGACTAGTTTACAAT-TCATCGTGAATGGCATC-3' (SEQ ID NO: 18), PCR was carried out to obtain a 1.7-kb DNA fragment containing a PDI1 gene having a Not I/Spe I restriction cleavage site and set forth in SEQ ID NO: 9. Then, the linearized pMK71 and the 1.7-kb DNA fragment were cleaved with Not I and Spe I, respectively, and the cleaved products were ligated to each other to construct a PDI1 gene expression vector which was designated pMPDI1 (FIG. 8). FIG. 8 illustrate restriction sites of a pMPDI1 expression vector adapted to allow co-expression of protein disulfide isomerase (PDI) by galactose, upon expression of a foreign protein in yeast.

6-1-2. Construction of PDI1?Co-Expression LK8 Producer Strain

Transformed yeast strains A and B were respectively transformed with the vector pMPDI1 constructed in Example 6-1-1. Transformation was carried out using Alkali Cation Yeast Transformation Kit (Q-BIO gene, Canada) according to manufacturer's instructions. The thus-transformed yeast strains were designated S. cerevisiae 2805/MδLK8/PDI and S. cerevisiae BJ3501/MδLK8/PDI, respectively.

6-2. Co-Expression Effects of PDI1 on Secretion of Foreign Proteins and Comparison Between Yeast Strains A and B In order to compare co-expression effects of the PDI1 gene on secretion of foreign proteins, transformed yeast strains A and B, and pMPDI1-transformed yeast strains A and B (S. cerevisiae 2805/MδLK8/PDI and S. cerevisiae BJ3501/MδLK8/PDI) were taken under storage at −70° C., and then fed-batch cultured in the same manner as in Example 3 to induce expression and secretion of the foreign proteins (see Table 3).

TABLE 3

Comparison of maximum extracellular secretion of foreign proteins in transformed yeast strains A and B with or without co-expression of PDI1 gene

| | S. cerevisiae 2805/MδLK8 | | S. cerevisiae BJ3501/MδLK8 | |
| --- | --- | --- | --- | --- |
| | Control[1] | Co-expression of PDI1 | Control | Co-expression of PDI1 |
| Maximum LK8 secretion (mg/L) | 100 | 130 | 250 | 430 |

[1] Control: without co-expression of PDI1

As can be seen in Table 3, S. cerevisiae 2805/MδLK8 exhibited LK8 secretion of 100 mg/L, whereas S. cerevisiae 2805/MδLK8/PDI1 exhibited LK8 secretion of 130 mg/L, thus representing that higher secretion of the foreign protein was achieved in S. cerevisiae 2805/MδLK8/PDI1.

Further, another yeast strain S. cerevisiae BJ3501/MδLK8 exhibited LK8 secretion of 250 mg/L, whereas S. cerevisiae BJ3501/MδLK8/PDI1 exhibited LK8 secretion of 430 mg/L, thus further showing that secretion of the foreign protein was higher in the yeast strain with co-expression of PDI1. That is, in two different strains, yeast strains with co-expression of PDI1 exhibited higher secretion amounts of LK8 than yeast strains without co-expression of PDI1.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

SEQUENCE LISTING

Sequence list is attached in electronic form

The invention claimed is:

1. A method for improving a secretion efficiency of a foreign protein, comprising the steps of:
   (a) transforming a yeast host with a recombinant foreign gene construct comprising a galactose-inducible promoter, a secretion signal sequence and a gene encoding the foreign protein to construct a transformed yeast host; and
   (b) culturing the transformed yeast strain under a condition that the activity of the galactose-inducible promoter is controlled,
   wherein the controlling of the activity of the galactose-inducible promoter is achieved by decreasing a transport rate of galactose from a culture medium into the transformed yeast host; and wherein the decreasing the transport rate of galactose from the medium into the transformed yeast host is achieved by rendering a galactose permease gene in the transformed yeast defective or partially disrupting said galactose permease gene to be non-functional.

2. The method according to claim 1, wherein the transforming of the step (a) is carried out by insertion of the recombinant foreign gene construct into a chromosome of the yeast host or by insertion of the recombinant foreign gene construct into a cytoplasm of the yeast host in the form of a circular vector.

3. The method according to claim 1, wherein the galactose-inducible promoter is a GAL1 promoter set forth in SEQ ID NO: 1, a GAL10 promoter set forth in SEQ ID NO: 2, or a GAL7 promoter set forth in SEQ ID NO: 3.

4. The method according to claim 1, wherein the condition that the activity of the galactose-inducible promoter is controlled in the step (b) is co-feeding of galactose and glucose in a given ratio to the culture medium during culturing.

5. The method according to claim 4, wherein the culturing is carried out by fed-batch culture.

6. The method according to claim 4, wherein the ratio of galactose and glucose is in the range of 4:1 to 1:1.

7. The method according to claim 1, wherein the yeast host is transformed with a recombinant foreign gene construct containing a protein disulfide isomerase-encoding gene that is expressed under the control of the galactose-inducible promoter.

8. The method according to claim 1, further comprising, between the steps (a) and (b), a step (a-1) of further transforming the transformed yeast strain of the step (a) with a protein disulfide isomerase-encoding gene that is expressed under the control of the galactose-inducible promoter.

9. The method according to claim 1, wherein the recombinant foreign gene construct further comprises a protein disulfide isomerase-encoding gene that is expressed under the control of the galactose-inducible promoter.

* * * * *

```
                        SEQUENCE LISTING

<160> NUMBER OF SEQ ID NOS: 18

<210> SEQ ID NO 1
<211> LENGTH: 453
<212> TYPE: DNA
<213> ORGANISM: Saccharomyces cerevisiae
<220> FEATURE:
<221> NAME/KEY: promoter
<222> LOCATION: (1)..(453)
<223> OTHER INFORMATION: GAL1 promoter

<400> SEQUENCE: 1
agtacggatt agaagccgcc gagcgggtga cagccctccg aaggaagact ctcctccgtg      60
cgtcctcgtc ttcaccggtc gcgttcctga aacgcagatg tgcctcgcgc cgcactgctc     120
cgaacaataa agattctaca atactagctt ttatggttat gaagaggaaa aattggcagt     180
aacctggccc cacaaacctt caaatgaacg aatcaaatta acaaccatag gatgataatg     240
cgattagttt tttagcctta tttctggggt aattaatcag cgaagcgatg attttttgatc    300 tattaacaga tatataaatg caaaaactgc ataaccactt taactaatac tttcaacatt     360
ttcggtttgt attacttctt attcaaatgt aataaaagta tcaacaaaaa attgttaata     420
tacctctata ctttaacgtc aaggagaaaa aac                                   453

<210> SEQ ID NO 2
<211> LENGTH: 507
<212> TYPE: DNA
<213> ORGANISM: Saccharomyces cerevisiae
<220> FEATURE:
<221> NAME/KEY: promoter
<222> LOCATION: (1)..(507)
<223> OTHER INFORMATION: GAL10 promoter

<400> SEQUENCE: 2
tcaaaaatca tcgcttcgct gattaattac cccagaaata aggctaaaaa actaatcgca      60
ttatcatcct atggttgtta atttgattcg ttcatttgaa ggtttgtggg gccaggttac     120
```

```
tgccaattt  tcctcttcat  aaccataaaa  gctagtattg  tagaatcttt  attgttcgga     180
gcagtgcggc  gcgaggcaca  tctgcgtttc  aggaacgcga  ccggtgaaga  cgaggacgca     240
cggaggagag  tcttccttcg  gagggctgtc  acccgctcgg  cggcttctaa  tccgtacttc     300
aatatagcaa  tgagcagtta  agcgtattac  tgaaagttcc  aaagagaagg  ttttttttagg    360 ctaagataat  ggggctcttt  acatttccac  aacatataag  taagattaga  tatggatagt     420
tatatggata  tgtatatggt  ggtaatgcca  tgtaatatga  ttattaaact  tctttgcgtc     480
catccaaaaa  aaaagtaaga  atttttg                                           507
```

```
<210> SEQ ID NO 3
<211> LENGTH: 625
<212> TYPE: DNA
<213> ORGANISM: Saccharomyces cerevisiae
<220> FEATURE:
<221> NAME/KEY: promoter
<222> LOCATION: (1)..(625)
<223> OTHER INFORMATION: GAL7 promoter

<400> SEQUENCE: 3
```

```
ggagttcagt  gataaaagtg  tcacagcgaa  tttcctcata  tgtagggacc  gaattgttta     60
caagttctct  gtaccaccat  ggagacatca  aagattgaaa  atctatggaa  agatatggac    120
ggtagcaaca  agaatatagc  acgagccgcg  gatttatttc  gttacttttg  atatcactca    180
caactattgc  gaagcgcttc  agtgaaaaaa  tcataaggaa  aagttgtaaa  tattattggt    240
actattcgtt  tggtaaagta  gagggggtaa  ttttttcccct  ttattttgtt  catacattct    300
taaattgctt  tgcctctcct  tttggaaagc  tatacttcgg  agcactgttg  agcgaaggct    360
cattagatat  attttctgtc  attttccttta  acccaaaaat  aagggagagg  gtccaaaaag    420
cgctcggaca  actgttgacc  gtgatccgaa  ggactggcta  tacagtgttc  acaaaatagc    480
caagctgaaa  ataatgtgta  gcctttagct  atgttcagtt  agtttggcta  gcaaagatat    540
aaaagcaggt  cggaaatatt  tatgggcatt  attatgcaga  gcatcaacat  gataaaaaaa    600
acagttgaat  attccctcaa  aaatg                                             625
```

```
<210> SEQ ID NO 4
<211> LENGTH: 85
<212> TYPE: PRT
<213> ORGANISM: Saccharomyces cerevisiae

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85
```

```
<210> SEQ ID NO 5
<211> LENGTH: 26
<212> TYPE: PRT
<213> ORGANISM: Saccharomyces cerevisiae
```

```
<400> SEQUENCE: 5

Met Thr Lys Pro Thr Gln Val Leu Val Arg Ser Val Ser Ile Leu Phe
 1               5                  10                  15

Phe Ile Thr Leu Leu His Leu Val Val Ala
            20                  25

<210> SEQ ID NO 6
<211> LENGTH: 19
<212> TYPE: PRT
<213> ORGANISM: Saccharomyces cerevisiae

<400> SEQUENCE: 6

Met Leu Leu Gln Ala Phe Leu Phe Leu Leu Ala Gly Phe Ala Ala Lys
 1               5                  10                  15

Ile Ser Ala

<210> SEQ ID NO 7
<211> LENGTH: 17
<212> TYPE: PRT
<213> ORGANISM: Kluyveromyces lactis

<400> SEQUENCE: 7

Met Asn Ile Phe Tyr Ile Phe Leu Phe Leu Leu Ser Phe Val Gln Gly
 1               5                  10                  15

Leu

<210> SEQ ID NO 8
<211> LENGTH: 48
<212> TYPE: PRT
<213> ORGANISM: Pichia acaciae

<400> SEQUENCE: 8

Met Leu Ile Ile Val Leu Leu Phe Leu Ala Thr Leu Ala Asn Ser Leu
 1               5                  10                  15

Asp Cys Ser Gly Asp Val Phe Phe Gly Tyr Thr Arg Gly Asp Lys Thr
            20                  25                  30

Asp Val His Lys Ser Gln Ala Leu Thr Ala Val Lys Asn Ile Lys Arg
        35                  40                  45

<210> SEQ ID NO 9
<211> LENGTH: 1569
<212> TYPE: DNA
<213> ORGANISM: Saccharomyces cerevisiae
<300> PUBLICATION INFORMATION:
<301> AUTHORS: Tachikawa, H. et al.
<302> TITLE: Molecular structure of a yeast gene, PDI1, encoding protein
      disulfide isomerase that is essential for cell growth
<303> JOURNAL: J. Biochem.
<304> VOLUME: 110
<305> ISSUE: 2
<306> PAGES: 306-313

<400> SEQUENCE: 9
atgaagtttt ctgctggtgc cgtcctgtca tggtcctccc tgctgctcgc ctcctctgtt     60
ttcgcccaac aagaggctgt ggcccctgaa gactccgctg tcgttaagtt ggccaccgac    120
tccttcaatg agtacattca gtcgcacgac ttggtgcttg cggagttttt tgctccatgg    180
tgtggccact gtaagaacat ggctcctgaa tacgttaaag ccgccgagac tttagttgag    240
aaaaacatta ccttggccca gatcgactgt actgaaaacc aggatctgtg tatggaacac    300
aacattccag ggtcccaag cttgaagatt ttcaaaaaca gcgatgttaa caactcgatc    360
gattacgagg gacctagaac tgccgaggcc attgtccaat tcatgatcaa gcaaagccaa    420
```

```
ccggctgtcg ccgttgttgc tgatctacca gcttaccttg ctaacgagac ttttgtcact      480
ccagttatcg tccaatccgg taagattgac gccgacttca acgccacctt ttactccatg      540
gccaacaaac acttcaacga ctacgacttt gtctccgctg aaaacgcaga cgatgatttc      600
aagctttcta tttacttgcc ctccgccatg gacgagcctg tagtatacaa cggtaagaaa      660
gccgatatcg ctgacgctga tgttttttgaa aaatggttgc aagtggaagc cttgccctac     720
tttggtgaaa tcgacggttc cgttttcgcc caatacgtcg aaagcggttt gccttt gggt     780 tacttattct acaatgacga ggaagaattg gaagaataca agcctctctt taccgagttg      840
gccaaaaaga acagaggtct aatgaacttt gttagcatcg atgccagaaa attcggcaga      900
cacgccggca acttgaacat gaaggaacaa ttccctctat ttgccatcca cgacatgact      960
gaagacttga agtacggttt gcctcaactc tctgaagagg cgtttgacga attgagcgac     1020
aagatcgtgt tggagtctaa ggctattgaa tctttggtta aggacttctt gaaaggtgat     1080
gcctccccaa tcgtgaagtc ccaagagatc ttcgagaacc aagattcctc tgtcttccaa     1140
ttggtcggta agaaccatga cgaaatcgtc aacgacccaa agaaggacgt tcttgttttg     1200
tactatgccc catggtgtgg tcactgtaag agattggccc caacttacca agaactagct     1260
gatacctacg ccaacgccac atccgacgtt ttgattgcta aactagacca cactgaaaac     1320
gatgtcagag gcgtcgtaat tgaaggttac ccaacaatcg tcttataccc aggtggtaag     1380
aagtccgaat ctgttgtgta ccaaggttca agatccttgg actctttatt cgacttcatc     1440
aaggaaaacg gtcacttcga cgtcgacggt aaggccttgt acgaagaagc ccaggaaaaa     1500
gctgctgagg aagccgatgc tgacgctgaa ttggctgacg aagaagatgc cattcacgat     1560
gaattgtaa                                                              1569

<210> SEQ ID NO 10
<211> LENGTH: 1601
<212> TYPE: DNA
<213> ORGANISM: Conus textile

<400> SEQUENCE: 10
gaattcgccc ttactaggat ccgcatcatc atgaagtttt catcttgttt agttttaact       60
cttctggttt ttgtatctgc cgaagatgtc gaacaggagg aaaatgtcca cgttttgacg      120
aagaaaaatt ttgactcctt cataactgat aatgagttcg tgcttgtgga atttt atgct      180 ccctggtgtg gccattgcaa ggcattggca ccagaatatg ccaaagctgc aacaactttg      240
gaaaacgaga agtcgaacat caagttggcc aaagtggatg ctactgtgga gggggatttg      300
gcctccaaat tgatgttcg tggatacccca acaatcaagt tcttccgtaa agagaagcct       360
gatggtccag cagactacag tggtggtcgc caagctaaag atattgttga ctggctgaag      420
aagaagacag gaccaccagc caaggaactg aaggagaaag atgaagtcaa ggcttttgtg      480
gaaaaagatg aagttgttgt cattggtttc ttcaaggatc aagaatccac aggtgctttg      540
gccttcaaaa aggcagctgc cggcattgat gacattccat tgccatcac ttcagaagat       600 catgttttca aggagtacaa gatggacaaa gatggcattg tactgctgaa gaagtttgat      660
gagggccgta atgacttcga ggggaatttg gaggaggagg aggccatcgt caagcacgtc      720
agggaaaacc aactgccact ggttgtgaa ttcactcaag agtctgccca agatctttt         780 ggaggtgagg tgaagaacca cattctgctg ttcctgaaga aggaaggtgg agaagacaca      840
attgaaaagt tcagaagtgc agctgaggat ttcaaaggaa aggtcctgtt tatctacttg      900
gacactgaca atgaggagaa tggacgcatc acagagttct ttggcttgaa ggatgatgaa      960
```

```
atcccagctg tgcgtctgat ccagctggca gaggacatgt caaagtacaa gcctgagtcc    1020
tcggatttgg aaactgccac catcaagaaa tttgtccagg atttcctgga tgggaaactg    1080
aagccccatc tgatgtctga ggatgtgcct ggtgactggg atgccaagcc tgtgaaggtc    1140
ctggtgggca agaacttcaa ggaagtggcg atggacaaat caaaggctgt ctttgtggag    1200
ttctatgctc cctggtgtgg acactgcaag cagctggccc ctatctggga tgagctgggt    1260
gaaaagtaca aggacagcaa ggacattgtt gttgccaaga tggatgccac tgccaatgag    1320
attgaagagg tcaaagtgca gagcttcccc accctcaagt acttcccaa ggacagcgag     1380 gaggctgtgg actacaatgg cgagagaacc ttggatgctt tcgttaaatt cctcgagagc    1440
ggtggcacgg aaggtgctgg agtgcaagag gatgaggaag aggaagagga agatgaggag    1500
ggtgatgatg aagatctgcc aagagatgaa ctgtagctgt catcggcatc tagactcgaa    1560
gggcgaattc cagcacactg gcggccgtta ctagtggatc c                        1601
```

<210> SEQ ID NO 11
<211> LENGTH: 1458
<212> TYPE: DNA
<213> ORGANISM: Caenorhabditis elegans
<300> PUBLICATION INFORMATION:
<301> AUTHORS: Page, A. P.
<302> TITLE: Cyclophilin and protein disulfide isomerase genes are
      co-transcribed in a functionally related manner in Caenorhabditis
      elegans
<303> JOURNAL: DNA Cell Biology
<304> VOLUME: 16
<305> ISSUE: 11
<306> PAGES: 1335-1343

<400> SEQUENCE: 11

```
atgtcactgt cagtgtcctt tatcttcctc ctggtcgcat caatcggagc agttgttgct     60
gacagcgaaa acgtgcttgt tctcactgaa agcaatttcg aagaaactat caatggaaat    120
gagtttgttc tagtcaaatt ctatgctcca tggtgtgtac attgcaagtc tcttgctcca    180
aagtacgacg aagccgccga tttgctgaag gaggaaggat ccgatatcaa gctcgccaag    240
gttgacgcca ccgaaaacca agctcttgca tccaagttcg aggtccgtgg atatccaact    300
atcctctact tcaagagtgg aaagccaacg aaatacaccg aggacgcgc caccgctcaa     360 attgtcgatt gggtcaagaa gaagagtgga ccaactgtta ccactgttga gtcagttgag    420
caactcgagg aattgaaggg aaagaccaga gttgttgttc ttggatactt caaggacgcg    480
aaatctgatg ctgctaccat ctacaacgaa gttgctgatt ctgtcgatga cgcattcttc    540
gccgttgccg gttctgctga ggttgctgct gccgcatctt tgaatgaaga tggagtcgct    600
cttatccgca ctgatggaga cgacagcgag actagcacaa ttgctgaagc tgaaatcacc    660
aacaccatcg ctcttaagca atggctccac gcttacaagc tctctgccgt gaccgagttc    720
acccacgaat ctgctcaaga aatcgtcgga ggagacctca aaaagttcca ctttttgatc    780
atccgcaagt cagactcttc tttcgatgag actattgcca agttcactga ggtcgctaag    840
aagttccgtg ctaagatcgt cttttgttctt ctcgacgttg atgttgaaga aacgcaaga    900 attctcgagt tcctcggagt cgatgccaag aacaccccag ccaacagaat tgtcagcctt    960
gccgatcaag ttgagaagtt caagccacaa gaaggagaag atttcgaagc tttccaccaa   1020
tcatatttgg aaggaaagtc tgctcaagac ttgaaggctc aagatcttcc agaagattgg   1080
aatgcactcc cagttaaggt tctcgtcgcc tccaacttca cgaaattgc ccttgatgaa     1140 accaagactg tcttcgtcaa attctacgcc ccatggtgcg acattgcaa gcaactggtt     1200
```

```
ccagtttggg atgagcttgc tgagaagtac gagtccaacc caaatgttgt cattgcaaag    1260
cttgatgcta ctctcaacga gcttgccgac gtcaaggtca actctttccc aaccctgaag    1320
ctgtggccag ccggatcttc taccccagtc gactatgatg agacagaaa cctcgagaag     1380 ttcgaagaat tgtcaacaa gtatgctgga tctgcttccg aatctgaaac cgcatctcag     1440
gatcacgaag agctttaa                                                  1458
```

<210> SEQ ID NO 12
<211> LENGTH: 1536
<212> TYPE: DNA
<213> ORGANISM: Homo sapiens
<300> PUBLICATION INFORMATION:
<301> AUTHORS: Desilva, M. G. et al.
<302> TITLE: Characterization and chromosomal localization of a new protein disulfide isomerase, PDIp, highly expressed in human pancreas
<303> JOURNAL: DNA Cell Biology
<304> VOLUME: 15
<305> ISSUE: 1
<306> PAGES: 9-16

<400> SEQUENCE: 12

```
atggcttcgt gccatggggg tcaggaacag ggagcgagga gccctcgga ggagcctcca      60 gaggaggaaa tccccaagga ggatgggatc ttggtgctga ccgccacac cctgggcctg     120 gccctgcggg agcaccctgc cctgctggtg gaattctatg ccccgtggtg tgggcactgc    180
caggccctgg cccccgagta cagcaaggca gctgccgtgc tcgcggccga gtcaatggtg    240
gtcacgctgg ccaaggtgga tgggcccgcg cagcgcgagc tggctgagga gtttggtgtg    300
acggagtacc ctacgctcaa gttcttccgc aatgggaacc gcacgcaccc cgaggagtac    360
acaggaccac gggacgctga gggcattgcc gagtggctgc gacggcgggt ggggcccagt    420
gccatgcggc tggaggatga ggcggccgcc caggcgctga tcggtggccg ggacctagtg    480
gtcattggct tcttccagga cctgcaggac gaggacgtgg ccaccttctt ggccttggcc    540
caggacgccc tggacatgac cttggcctc acagaccggc cgcggctctt tcagcagttt     600
ggcctcacca aggacactgt ggttctcttc aagaagtttg atgaggggcg gcagacttc     660 cccgtggacg aggagcttgg cctggacctg ggggatctgt cgcgcttcct ggtcacacac    720
agcatgcgcc tggtcacgga gttcaacagc cagacgtctg ccaagatctt cgcggccagg    780
atcctcaacc acctgctgct gtttgtcaac cagacgctgg ctgcgcaccg ggagctccta    840
gcgggctttg ggaggcagc tccccgcttc cgggggcagg tgctgttcgt ggtggtggac    900
gtggcggccg acaatgagca cgtgctgcag tactttggac tcaaggctga ggcagccccc    960
actctgcgct tggtcaacct tgaaaccact aagaagtatg cgcctgtgga tgggggccct   1020
gtcaccgcag cgtccatcac tgcttttcgc catgcagtcc tcaacggcca agtcaagccc   1080
tatctcctga gcaggagat accccctgat tgggatcagc ggccagttaa gaccctcgtg    1140
ggcaagaatt ttgagcaggt ggcttttgac gaaaccaaga atgtgtttgt caagttctat   1200
gccccgtggt gcacccactg caaggagatg gcccctgcct gggaggcatt ggctgagaag   1260
taccaagacc acgaggacat catcattgct gagctggatg ccacgccaa cgagctggat    1320 gccttcgctg tgcacggctt ccctactctc aagtacttcc cagcagggcc aggtcggaag   1380
gtgattgaat acaaaagcac cagggacctg agactttct ccaagttcct ggacaacggg    1440
ggcgtgctgc ccacggagga gtccccggag gagccagcag ccccgttccc ggagccaccg   1500
gccaactcca ctatggggtc caaggaggaa ctgtag                              1536
```

<210> SEQ ID NO 13
<211> LENGTH: 1547
<212> TYPE: DNA
<213> ORGANISM: Aspergillus oryzae

<400> SEQUENCE: 13

| | | | | | | |
|---|---|---|---|---|---|---|
| atgcggactt | tcgcacccttg | gatcttgagc | cttctagggg | cttctgctgt | agcttctgct | 60 |
| gccgatgcga | ctgccgaagc | tccctccgat | gtggtctcgc | tcaccgggga | cacattcgaa | 120 |
| actttcgtca | aggagcatga | cctagttttg | gccgagtttt | ttgctccctg | gtgtggccat | 180 |
| tgcaaggctc | tcgctccgaa | atacgagcag | gccgccactg | agttaaagga | aagaacatt | 240 |
| ccgctggtca | aggttgattg | caccgaggaa | gaggctcttt | gtagggacca | aggtgttgaa | 300 |
| ggttacccca | cgctgaagat | tttccgtggc | cttgacgctg | ttaagcctta | tcagggagct | 360 |
| cgtcagaccg | aggcgattgt | ttcatacatg | gtcaagcagt | cactacctgc | tgtgtcccct | 420 |
| gtcaccccag | aaaacctcga | agagatcaag | actatggaca | agattgtcgt | tattggttat | 480 |
| atcgcgtctg | acgaccagac | tgccaatgat | atattcacca | cttttgccga | gtcacagaga | 540 |
| gacaactacc | tcttcgccgc | cacaagtgat | gcatcgatcg | ctaaggcaga | aggtgttaag | 600 |
| caaccttcga | ttgttctcta | taaagacttc | gatgaaaaga | aagctactta | tgatggagag | 660 |
| attgaacagg | atgccctcct | cagttgggtc | aagactgcca | gtaccccctt | ggtgggcgag | 720 |
| ctgggcccag | agacttactc | cggatatata | acggctggca | ttccactggc | gtacattttc | 780 |
| gccgaaacca | agaagagcg | tgagcagttc | accgaggagt | tcaagttcat | cgccgagaaa | 840 |
| cacaagggtt | ccatcaatat | tgtcaccatt | gacgccaagt | gtacggcgc | tcatgcaggc | 900 |
| aatctcaacc | ttgacccctc | caagttccct | gcattcgcta | ttcaagaccc | tgaaaagaac | 960 |
| gccaagtatc | cttatgacca | gtcgaaggaa | gtcaaggcca | aggatatcgg | taaattcatc | 1020 |
| caagacgttc | ttgatgataa | agtagagcca | agcattaagt | ctgaggctat | tcctgagact | 1080 |
| caggaaggtc | ctgttactgt | tgttgtcgcg | cattcctata | aggatctcgt | ccttgacaac | 1140 |
| gagaaggacg | tccttctcga | attttatgcg | ccatggtgcg | acactgcaa | ggcccttgcc | 1200 |
| ccgaagtacg | aggaacttgc | aagcctttac | aaggatattc | tgaagttac | catcgccaaa | 1260 |
| attgacgcaa | cggccaacga | tgtccccgac | tccattacag | gatttcctac | tattaagctc | 1320 |
| ttcgctgccg | gcgccaagga | ctccccagtt | gaatatgaag | gctctcgcac | ggtggaggac | 1380 |
| ctcgccaact | tcgtcaagga | gaatggcaag | cacaaggtcg | atgctcttga | agttgatccg | 1440 |
| aagaaagaac | aggagagtgg | cgatgccacc | gagactcggg | ccgcctctga | cgagaccgaa | 1500 |
| actcctgctg | ctactagcga | tgacaagtct | gagcatgatg | aattgta | | 1547 |

<210> SEQ ID NO 14
<211> LENGTH: 1593
<212> TYPE: DNA
<213> ORGANISM: Candida boidinii

<400> SEQUENCE: 14

| | | | | | | |
|---|---|---|---|---|---|---|
| atgaagttaa | ctaatttcaa | agttattgcc | acaattcttg | cttgtttaac | agttgttaga | 60 |
| gctgatgatg | gtggtgccat | tgcatctcca | gattccgctg | ttgttaaatt | aactgctgat | 120 |
| tcattcgaat | cattcatgaa | agaaaatcca | ttagtcttag | ctgaattttt | tgctccttgg | 180 |
| tgtggtcatt | gtaaaagatt | gggtcctgaa | tttcaagttc | tgctgataa | attagttgaa | 240 |
| aaagatatta | gattagctca | aattgattgt | accgaagaaa | aagatttatg | ttcttcttat | 300 |
| ggtattaaag | gttacccaac | tttaaaagtc | tttagaggtt | acgaaaatga | accttctgat | 360 |
| tatgctggtc | aaagaacttc | agattcaatc | atttcttata | tggttaaaca | atcaacccca | 420 |

```
cctgtctcca tcgttgatga tctctcagat atcgaagata caattaaaga atcaaatgat      480
cctgtcttta ttcaagtctt accaaaaggt tctaaatctg ttgaagccgg taactcaact      540
ttctttgaaa tcgctaatgg tttaagagat aactactctt ttatttcaac aacaagtact      600
gaattctctt caaaatactt gaaaggtatt aaaaaatcag atactccatc ttatattctc      660
tttagaccaa atgaagaatt gtctgatgct tcaatctata aatttgatga aattgatgat      720
actcatttaa tcgaattctt aaacgttgaa tcaaaacctt tattcggtga atggatggt       780 tcttctttcc aatcttatat ggaaatgaaa ttaccagttg cttattattt ctataatgaa      840
atctctgaaa aagatgccgt ctctgatgcc atcagtaaat tagctaaaac tcatagaggt      900
aaagttaatt tcgttggttt agacgcttct aaatatggtt tacacgctaa gaatattaac      960
atgaaggaag aattccctct tttcgctatt cacgatttag caactgaatt aaaatacggt     1020
atctcccaag ataaaccatt agataataaa ttaattccaa aattcgttga agatttcgtt     1080
gctggtaaat tagaagcaat cattaaatca gaaccaatcc cagaaactca agattctcca     1140
gtttaccatt tagtcggtaa agaacatgat aaaattatta cctctgataa agatgtctta     1200
gttaaatatt acgctccatg gtgtggtcac tgtaaaaaat tagctccagt ctttgaagaa     1260
ttagctgctg tttatgaatc agttgctcca ggtaaagtct tattagctga tttagatcat     1320
actgaaaatg atgtcaccgg tgttcacatt gaaggttacc caactatcgt cttataccca     1380
gccgatggtt cagaaccagt tgtttacgaa ggtaacagat cttttgaatc tttctccgat     1440
ttcattaaag aaaaaggttc atcaggtgtt gatgctaatg cattaaaaga accttaccca     1500
gaagaaggta ctgaaggtgc tccagttgat ccagaatcag ttggtgatgc tgaaaaagaa     1560
gatgattctg ctgctgatgt tcgtgatgaa tta                                  1593

<210> SEQ ID NO 15
<211> LENGTH: 1518
<212> TYPE: DNA
<213> ORGANISM: Humicola insolens

<400> SEQUENCE: 15
atgcataagg cccagaagtt cgcgctcggc ctgcttgccg cggcggcagt tgccacagct       60
tcggatgttg tccagctgaa gaaggacacc ttcgacgact tcatcaagac gaatgacctt      120
gttctcgccg aattcttcgc gccgtggtgc ggtcactgca aggctctcgc ccccgagtac      180
gaggaggctg cgaccacact gaaggagaag aacatcaagc tcgccaaggt ggactgcaca      240
gaggagacgg acctctgcca caacatggtt gttgagggct acccgactct caaggtcttc      300
cgcggccttg acaacgtctc cccctacaag ggccagcgca aggctgctgc tatcacctcg      360
tacatgatca agcagtctct gcccgccgtg tccgaggtca cgaaggacaa cctggaggag      420
ttcaagaagg ccgacaaggc cgtccttgtc gcctatgtgg atgcttccga caaggcgtcc      480
agtgaggttt tcacccaggt cgccgagaag ctgcgcgaca actacccgtt cggctccagc      540
agcgatgctg cgctggccga ggctgagggc gtcaaggctc ccgctatcgt cctttacaag      600
gactttgatg agggcaaggc ggtcttctcc gagaagttcg aggtggaggc gatcgagaag      660
ttcgccaaga cgggcgccac cccgctcatt ggcgagattg ccccgaaaac ctactccgac      720
tacatgtcgg ccggcatccc tctggcctac attttcgccg aaacggccga ggagcggaag      780
gagctcagcg acaagctcaa gccgatcgcc gaggctcagc gcggcgtcat taactttggt      840
actattgacg ccaaggcttt tggtgcccac gccggcaacc tgaacctgaa gaccgacaag      900
ttccccgcct tcgccatcca ggaggtcgcc aagaaccaga agttccccctt cgatcaggag      960
```

```
aaggagatca ccttcgaggc gatcaaggct ttcgtcgacg actttgtcgc cggtaagatc      1020
gagcccagca tcaagtcgga gccgatccct gagaagcagg agggcgccgt caccgtcgtc      1080
gttgccaaga actacaatga gatcgtcctg gacgacacca aggatgtgct gattgagttc      1140
tacgccccgt ggtgcggcca ctgcaaggcc ctggctccca agtacgagga gctcggcgcc      1200
ctgtatgcca agagcgagtt caaggaccgg gtcgtcatcg ccaaggttga tgccacggcc      1260
aacgacgttc ccgatgagat ccagggattc cccaccatca agctgtaccc ggccggtgcc      1320
aagggtcagc ccgtcaccta ctctggctcg cgcactgtcg aggacctcat caagttcatc      1380
gccgagaacg gcaagtacaa ggccgccatc tcggaggatg ccgaggagac gtcgtccgca      1440
accgagacga ccaccgagac ggccaccaag tcggaggagg ctgccaagga cacggcgacg      1500
gagcacgacg agctctag                                                    1518

<210> SEQ ID NO 16
<211> LENGTH: 258
<212> TYPE: DNA
<213> ORGANISM: Homo sapiens
<220> FEATURE:
<221> NAME/KEY: gene
<222> LOCATION: (1)..(258)
<223> OTHER INFORMATION: LK8 cDNA

<400> SEQUENCE: 16
gaacaggact gcatgtttgg gaatgggaaa ggataccggg gcaagaaggc aaccactgtt        60
actgggacgc catgccagga atgggctgcc caggagcccc atagacacag cacgttcatt       120
ccagggacaa ataaatgggc aggtctggaa aaaaattact gccgtaaccc tgatggtgac       180
atcaatggtc cctggtgcta cacaatgaat ccaagaaaac ttttttgacta ctgtgatatc      240 cctctctgtg catcctct                                                    258

<210> SEQ ID NO 17
<211> LENGTH: 39
<212> TYPE: DNA
<213> ORGANISM: Artificial
<220> FEATURE:
<223> OTHER INFORMATION: Synthetic construct

<400> SEQUENCE: 17
ataagaatgc ggccgccata catctatccc gttatgaag                              39

<210> SEQ ID NO 18
<211> LENGTH: 32
<212> TYPE: DNA
<213> ORGANISM: Artificial
<220> FEATURE:
<223> OTHER INFORMATION: Synthetic construct

<400> SEQUENCE: 18
ggactagttt acaattcatc gtgaatggca tc                                     32
```